US011911661B2

(12) United States Patent
Beaudouin et al.

(10) Patent No.: US 11,911,661 B2
(45) Date of Patent: Feb. 27, 2024

(54) SYSTEMS AND METHODS FOR SENSOR-BASED SPORTS ANALYTICS

(71) Applicant: GAMECHANGER ANALYTICS, INC., Palo Alto, CA (US)

(72) Inventors: Ralph Beaudouin, East Palo Alto, CA (US); Victor Boswell Hudson, Palo Alto, CA (US); Stefan George Lyzwa, Palo Alto, CA (US); Omotaye Sayre Martins, San Francisco, CA (US); Miles Victor Hudson, Palo Alto, CA (US); Sebastian Mateo Reed Beaudouin, East Palo Alto, CA (US); Zander Rafael Reed Beaudouin, East Palo Alto, CA (US)

(73) Assignee: GameChanger Analytics, Inc., Palo Alto, CA (US)

( * ) Notice: Subject to any disclaimer, the term of this patent is extended or adjusted under 35 U.S.C. 154(b) by 0 days.

(21) Appl. No.: 18/152,323

(22) Filed: Jan. 10, 2023

(65) Prior Publication Data

US 2023/0191199 A1    Jun. 22, 2023

Related U.S. Application Data

(63) Continuation of application No. PCT/US2021/070859, filed on Jul. 9, 2021.
(Continued)

(51) Int. Cl.
*A63B 24/00* (2006.01)
*A63B 63/00* (2006.01)
(Continued)

(52) U.S. Cl.
CPC ........ *A63B 24/0062* (2013.01); *A63B 63/004* (2013.01); *A63B 63/083* (2013.01);
(Continued)

(58) Field of Classification Search
CPC . A63B 24/0062; A63B 63/004; A63B 63/083; A63B 71/0622; A63B 2071/0655;
(Continued)

(56) References Cited

U.S. PATENT DOCUMENTS

| | | | | |
|---|---|---|---|---|
| 9,526,946 B1* | 12/2016 | Zets | ................... | G09B 19/0038 |
| 2003/0163287 A1* | 8/2003 | Vock | ................. | H04M 1/72412 |
| | | | | 702/187 |

(Continued)

FOREIGN PATENT DOCUMENTS

| | | |
|---|---|---|
| EP | 2945143 A1 | 11/2015 |
| JP | 2012139493 A | 7/2012 |

(Continued)

OTHER PUBLICATIONS

International Search Report and Written Opinion dated Dec. 2, 2021; International Application No. PCT/US2021/070859; 16 pages.

*Primary Examiner* — Jeffrey S Vanderveen
(74) *Attorney, Agent, or Firm* — FORTEM IP LLP; Matthew V. Lincicum

(57) ABSTRACT

Systems and methods for sports analytics are disclosed. A system for evaluating athletic performance can include wearable sensor devices configured to be removably coupled to an athlete's body during athletic performance, and one or more equipment-mountable sensor devices configured to be coupled to reference objects adjacent to an athletic performance site such as a goal or equipment. A computing device can be communicatively coupled to the wearable sensor device(s) and the equipment-mountable sensor device(s). The computing device is configured to receive sensor data from each of the sensor device(s) and to determine at least one performance parameter.

25 Claims, 15 Drawing Sheets

Related U.S. Application Data

(60) Provisional application No. 62/705,704, filed on Jul. 10, 2020.

(51) Int. Cl.
*A63B 63/08* (2006.01)
*A63B 71/06* (2006.01)

(52) U.S. Cl.
CPC .. *A63B 71/0622* (2013.01); *A63B 2071/0655* (2013.01); *A63B 2220/803* (2013.01); *A63B 2220/805* (2013.01); *A63B 2220/833* (2013.01); *A63B 2220/836* (2013.01); *A63B 2225/50* (2013.01)

(58) Field of Classification Search
CPC ........ A63B 2220/803; A63B 2220/805; A63B 2220/833; A63B 2220/836; A63B 2225/50
See application file for complete search history.

(56) References Cited

U.S. PATENT DOCUMENTS

| | | | |
|---|---|---|---|
| 2009/0256677 A1 | 10/2009 | Hein et al. | |
| 2015/0195099 A1* | 7/2015 | Imes | H04L 12/2827 |
| | | | 700/275 |
| 2017/0239551 A1 | 8/2017 | Pease et al. | |
| 2018/0036616 A1 | 2/2018 | Mckenney | |
| 2019/0118036 A1* | 4/2019 | Molyneux | G01S 13/34 |
| 2020/0054929 A1* | 2/2020 | Ward | A63B 24/0021 |

FOREIGN PATENT DOCUMENTS

| | | | |
|---|---|---|---|
| WO | 2019104388 A1 | 6/2019 | |
| WO | WO-2019104388 A1 * | 6/2019 | ........... G01C 21/165 |
| WO | 2019161277 A1 | 8/2019 | |

* cited by examiner

SYSTEMS AND METHODS FOR SENSOR-BASED SPORTS ANALYTICS

CROSS-REFERENCE TO RELATED APPLICATIONS

This application is a continuation of International Application No. PCT/US2021/070859, filed Jul. 9, 2021, which claims priority to U.S. Provisional Application No. 62/705,704, filed Jul. 10, 2020, each of which is hereby incorporated by reference in its entirety.

TECHNICAL FIELD

The present technology relates to wearable and stationary or equipment-mountable sensor devices and associated systems and methods of use. In particular, embodiments of the present technology are directed to systems and devices for motion capture, data processing, and feedback related to sports analytics.

BACKGROUND

In the context of team or individual sports, athletic development and performance are comprised of the following areas: technical, tactical, physical, and emotional. Sports analytics currently uses sensor technology or video analysis to offer detailed information pertaining to game tactics and athlete fitness to assist in managing both individual and group performances. Acquired data can be used for optimization of exercise programs and development of nutrition plans and team strategies. Such sensors are often bulky and unsuitable to being worn during athletic performance. Additionally, existing approaches do not address all areas of athletic performance and development. Accordingly, there is a need for improvement in wearable sensor technology for enabling advances in all areas of athletic development and performance.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

I. Overview

Figure 1A:
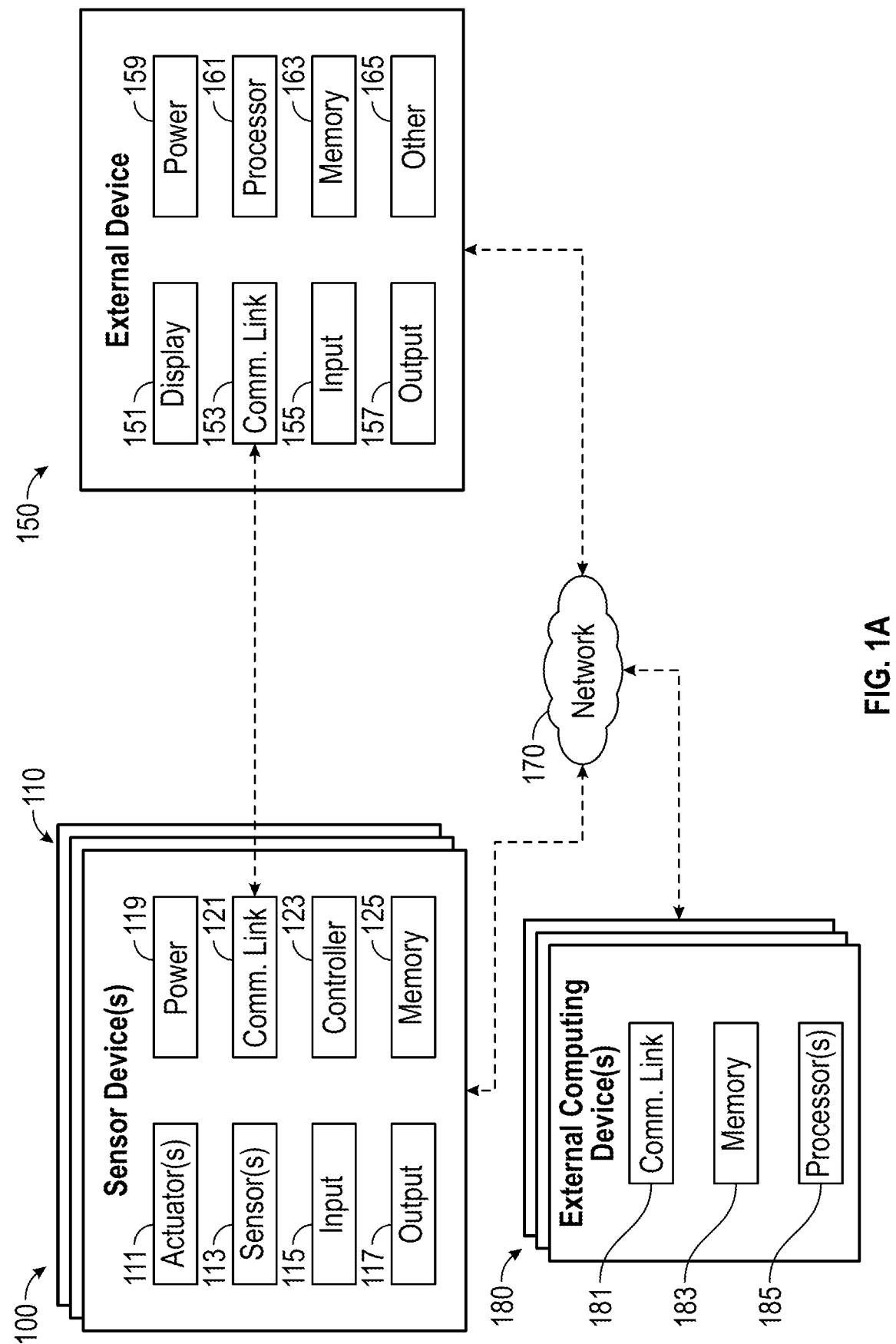
FIG. 1A is a block diagram of an example sensor device in accordance with the present technology.

The present technology relates to sensor technology and associated systems and methods of use. Some embodiments of the present technology, for example, are directed to inertial measurement units. Specific details of several embodiments of the technology are described below with reference to FIGS. 1A-13B.

Existing sports analytics techniques rely on video analysis and/or bulky sensors that are unsuitable for use during athletic performance. Embodiments of the present technology can provide for improved sensing and analysis of athletic performance. In particular, the present technology can leverage technological advancements in hardware and software to obviate the ubiquitous use of video along with its stringent requirements. 3D motion capture using inertial measurement units can be used to generate data from which an athlete's technical efficiency and efficacy can be gleaned. Optimization in this area has a major impact on individual rate of development and, ultimately, individual and team performance, respectively.

In some embodiments, the present technology can evaluate an athlete's technical prowess through biomechanical analysis via 3D motion capture, monitoring the rotational and translational movements of the body and the associated forces. Insights gleaned from this can lead to adjustments in athletic training thereby enhancing individual development and performance.

Although particular examples are provided below in the context of soccer, basketball, and track and field, embodiments of the present technology can be applied to a wide variety of activities. Examples include baseball, football, volleyball, lacrosse, dance, figure skating, speed skating, boxing, martial arts, physical therapy, golf, bowling, hockey, gymnastics, and others.

II. Example Systems for Evaluating Athletic Performance

Sensing System Overview

The following discussion provides a brief, general description of a suitable environment in which the present technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g., a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1A is a schematic diagram of sensor system 100 configured in accordance with an embodiment of the disclosed technology. Although the system 100 is shown with certain devices for purposes of explanation, in various examples any one or more of the devices shown in FIG. 1A can be omitted. Similarly, although the devices shown in FIG. 1A are illustrated as including certain components, in various examples any one or more of the particular components within these devices can be omitted (e.g., the sensor device 110 may omit the actuators 111). Moreover, any of the devices can include additional components not specifically shown here.

In the illustrated embodiment, the sensor device 110 comprises one or more vibration actuator(s) 111, one or more sensor(s) 113, input 115, output 117, a power source 119, a communications link 121, a controller 123, and a memory 125. The sensor device 110 is configured to be coupled to a user for sensing performance parameters of a user (e.g., during athletic performance). For example, the sensor device 110 may be removably worn by the user, for example positioned directly over the user's ankle or wrist and held in place via a band or other fastener. Additionally or alternatively, the sensor device 110 can be mounted to a stationary object, such as a piece of sports equipment (e.g., soccer goal, basketball backboard, etc.).

The vibration actuator(s) 111 can be any suitable component or combination of components configured to supply vibrational energy to be provided as a form of haptic feedback or output to the athlete. For example, in various examples, the vibration actuator(s) 111 can include a piezoelectric actuator, a speaker, or any other suitable actuator capable of delivering vibrational energy. For example, when an athlete performs a particular motion (e.g., swinging a baseball bat) in a correct (or incorrect) manner, vibrational output can be provided in real-time or near-real-time as form of feedback to the athlete. In some embodiments, the particular form of vibrational output can vary depending on the other sensed parameters. For example, when an athlete performs a particular motion incorrectly (e.g., serving a tennis ball, punching a boxing bag, etc.), the vibrational output can have a particular pattern that indicates one type of error, and a different pattern that indicates another type of error. The vibrational patterns can vary in one or more of intensity, duration, pulse width, duty cycle, frequency, or any other suitable aspect of the vibrational patterns.

The sensor(s) 113 can include a number of different sensors and/or types of sensors. For example, the sensor(s) 113 can include one or more of an electrode, accelerometer, magnetometer, pressure sensor, gyroscope, a blood pressure sensor, a pulse oximeter, an ECG sensor or other heart-recording device, an EMG sensor or other muscle-activity recording device, a temperature sensor, a skin galvanometer, hygrometer, altimeter, proximity sensor, hall effect sensors, or any other suitable sensor for monitoring performance or movement characteristics of the user. These particular sensors are exemplary, and in various embodiments, the sensors employed can vary.

In some embodiments, the power source 119 can be rechargeable, for example using inductive charging or other wireless charging techniques. Such rechargeability can facilitate long-term placement of the sensor device 110 on or about a user. The input 115 and output 117 components can include, for example, one or more buttons, keys, lights, microphones, speakers, ports (e.g., USB-C connector ports), etc.

In various embodiments, the memory 125 can take the form of one or more computer-readable storage modules configured to store information (e.g., signal data, subject information or profiles, environmental data, treatment regimes, data collected from one or more sensing components, media files) and/or executable instructions that can be executed by the controller 123. The memory 125 can include, for example, instructions for causing the sensors 113 to initiate data collection, to analyze sensor data to evaluate the user's athletic performance, etc. In some embodiments, the memory 125 stores data (e.g., sensor data acquired from the sensor(s) 113) used in the feedback techniques disclosed herein.

The communications link 121 enables the sensor device 110 to transmit to and/or receive data from external devices (e.g., external device 150 or external computing devices 180). The communications link 121 can include a wired communication link and/or a wireless communication link (e.g., Bluetooth, Near-Field Communications, LTE, 5G, Wi-Fi, infrared and/or another wireless radio transmission network).

The controller 123 can include, for example, a suitable processor or central processing unit ("CPU") that controls operation of the sensor device 110 in accordance with computer-readable instructions stored on the memory 125. The controller 123 may be any logic processing unit, such as one or more CPUs, digital signal processors (DSPs), application-specific integrated circuits (ASICs), etc. The controller 123 may be a single processing unit or multiple processing units in a device or distributed across multiple devices. The controller 123 is connected to the memory 125 and may be coupled to other hardware devices, for example, with the use of a bus (e.g., a PCI Express or Serial ATA bus). The memory 125 can include read-only memory (ROM) and random-access memory (RAM) or other storage devices, such as disk drives or SSDs, that store the executable applications, test software, databases, and other software required to, for example, implement the various routines described herein, control device components, communicate and exchange data and information with remote computers and other devices, etc.

The controller 123 also includes drive circuitry configured to control operation of the vibration actuator(s) 111 of the sensor device 110. For example, the drive circuitry can be configured to deliver waveforms having predetermined and controllable parameters to one or more of vibration actuator(s) 111. The controller 123 can also be configured to initiate data collection via one or more sensor(s) 113. For example, the sensor(s) 113 of the sensor device 110 can detect physiological and/or performance data of a user (e.g., motion data). In some embodiments, this performance data can be used in a feedback loop to affect operation of the vibration actuator(s) 111 and to improve the use's performance and rate of development of particular techniques, forms, or other aspects of athletic performance.

The sensor device 110 can be communicatively coupled to an external device 150, for example via a wireless connection. In some embodiments, the external device 150 can be a mobile device (e.g., a smartphone, tablet, smartwatch, etc.) or other computing devices with which the user can interact. In operation, the sensor device 110 may receive input from and/or can be controlled by instructions from the external device 150. For example, the external device 150 can cause the sensor device 110 to initiate or cease data collection and/or provide other control instructions to the sensor device 110. Additionally or alternatively, the external device 150 may output user prompts which can be synchronized with data collection via the sensor device 110. For example, the external device 150 may instruct the user to perform a particular drill, motion, etc., and the sensor device 110 may record performance data (e.g., via sensor(s) 113) while the user performs the requested actions.

The sensor device 110 and/or the external device 150 can also be communicatively coupled with one or more external computing devices 180 (e.g., over network 170). In some examples, the external computing devices 180 can take the form of servers, personal computers, tablet computers, or other computing devices associated with one or more data analytics providers. These external computing devices 180 can collect data recorded by the sensor device 110 and/or the external device 150. In some embodiments, such data can be anonymized and aggregated to perform large-scale analysis (e.g., using machine-learning techniques or other suitable data analysis techniques) to develop and improve algorithms using data collected by a large number of sensor devices 110. Additionally, the external computing devices 180 may transmit data to the external device 150 and/or the sensor device 110. For example, an updated algorithm for evaluating athletic performance for one or more sports or activities may be developed by the external computing devices 180 (e.g., using machine learning or other techniques) and then provided to the sensor device 110 and/or the external device 150 via the network (e.g., as an over-the-air update), and installed on the sensor device 110 and/or external device 150.

The sensor device 110 may be configured to calculate performance characteristics relating to one or more signals received from the sensor(s) 113. For example, the sensor device 110 may be configured to algorithmically determine an athlete's movement, position, orientation, gait, etc. In certain embodiments, the sensor device 110 initiates delivery of vibrational energy via the actuators 111 in response to sensor data (e.g., upon detecting proper or improper movement by the athlete). In some embodiments, the sensing performed via the sensor(s) 113 can be modified in response to event detection, for example with an increased sampling rate or other modification.

As noted above, in some embodiments, the sensor device 110 may also communicate with an external device 150. The external device 150 can be, for example, a smartwatch, smartphone, laptop, tablet, desktop PC, or any other suitable computing device and can include one or more features, applications, and/or other elements commonly found in such devices. For example, the external device 150 can include display 151, a communications link 153 (e.g., a wireless transceiver that may include one or more antennas for wirelessly communicating with, for example, other devices, websites, and the sensor device 110). Communication between the external device 150 and other devices can be performed via, e.g., a network 170 (which can include the Internet, public and private intranet, a local or extended Wi-Fi network, cell towers, the plain old telephone system (POTS), etc.), direct wireless communication, Bluetooth, NFC, etc. The external device 150 can additionally include well-known input components 131 and output components 133, including, for example, a touch screen, a keypad, speakers, a camera, etc.

In operation, the user may receive output or instructions from the external device 150 that are based at least in part on data received at the external device 150 from the sensor device 110. For example, the sensor device 110 may generate feedback based on analysis of data collected via sensor(s) 113. The sensor device 110 may then instruct the external device 150 to output an alert to the user (e.g., via display 151 and/or output 157) or another entity. In some embodiments, the alert can both be displayed to the user (e.g., via display 151 of the external device) and can also be transmitted to appropriate recipients. In some embodiments, embedded circuitry that provides location data (e.g., a GPS unit) can be included within the sensor device 110.

Additionally or alternatively, the external device 150 may output user prompts which may be used in conjunction with physiological data collection via the sensor device 110. For example, the external device 150 may instruct the user to perform an action (e.g., perform a particular drill), and the external device 150 may record activity data while the user performs the requested actions. In some embodiments, the external device 150 may itself analyze performance parameters of the user, for example using a camera to monitor a user's performance. In some embodiments, such physiological data collected via the external device 150 can be combined with data collected via the sensor(s) 113 and analyzed together to make a determination of a user's performance. Additionally or alternatively, the external device 150 can be used to display a real-time 3D rendering of the recorded activity for analysis by coach and/or trainer.

As noted previously, the external computing device(s) 180 can take the form of servers or other computing devices associated with data analytics providers or other entities. The external devices can include a communications link 181 (e.g., components to facilitate wired or wireless communication with other devices either directly or via the network 170), a memory 183, and processing circuitry 185. These external computing devices 180 can collect data recorded by the sensor device 110 and/or the external device 150. In some embodiments, such data can be anonymized and aggregated to perform large-scale analysis (e.g., using machine-learning techniques or other suitable data analysis techniques) to develop and improve sensing and analytical algorithms using data collected by a large number of treatment devices 110 associated with a large population of users. Additionally, the external computing devices 180 may transmit data to the external device 150 and/or the sensor device 110. For example, an updated algorithm for evaluating athletic performance may be developed by the external computing devices 180 (e.g., using machine learning or other techniques) and then provided to the sensor device 110 and/or the external device 150 via the network 170, and installed on the recipient sensor device 110.

Figure 1B:
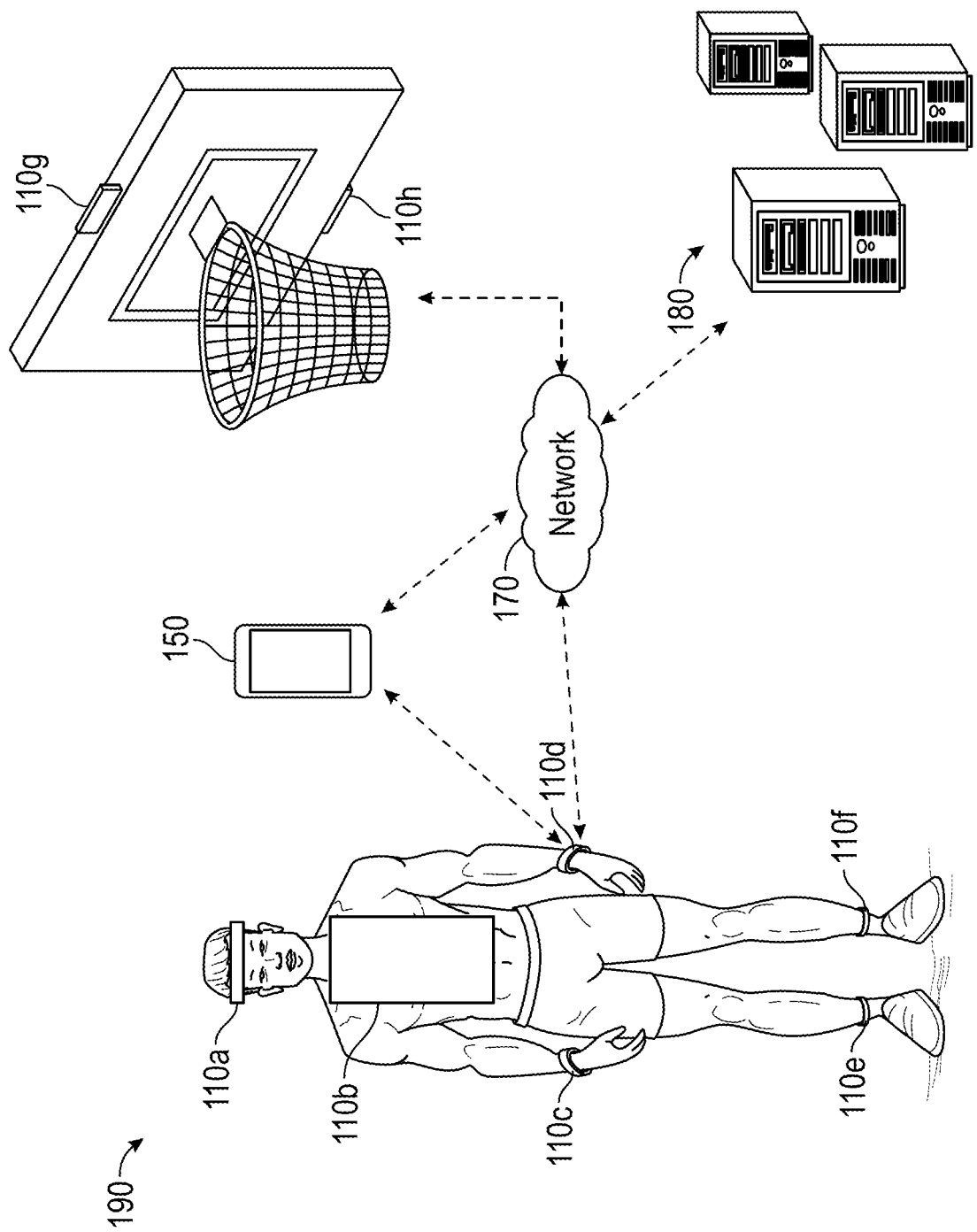
FIG. 1B is a schematic diagram of an example sensor network and environment in accordance with the present technology.

FIG. 1B illustrates a schematic view of the system 100, in which a plurality of wearable sensor devices 110*a-f* are disposed about a user 190 (e.g., around the user's head, torso, wrists, ankles, elbows, arms, thighs, knees, waist, etc.) for tracking various aspects of the user's performance during athletic activities. In addition, stationary sensor devices 110*g* and 110*h* are mounted to equipment (in this example, a basketball backboard). Each of the sensor devices 110 can communicate with one another (directly or indirectly) and with the additional external devices 150 and/or 180 to detect, monitor, and analyze athletic performance of the user 190.

Figure 2:
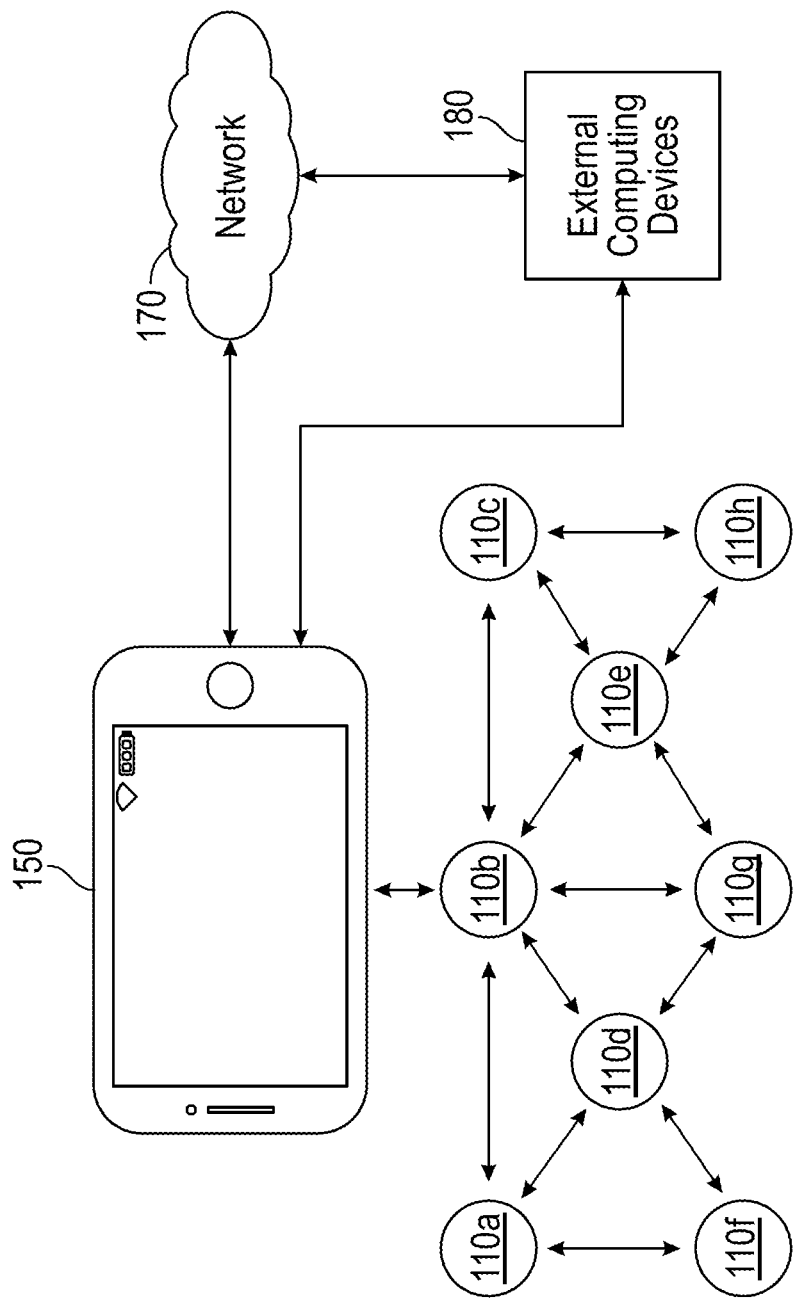
FIG. 2 illustrates an example computing environment suitable for implementing the present technology.

FIG. 2 illustrates an example for the implementation of the system architecture. In particular embodiments, the external device 150 may be the gateway and sensor devices 110*a*-110*h*, by way of example and not limitation, may be a combination of the sensor devices disclosed herein. All devices within the same mesh may communicate with each other, either directly or via one or more intermediate devices. Data transfer may take place, by way of example and not limitation, between the individual sensor devices 110*a-h* and the external device 150 or gateway.

In some embodiments, the external device 150 can be a mobile device (e.g., a smartphone, tablet, etc.). The mobile device can include one or more features, applications, and/or other elements commonly found in smartphones and other know mobile devices. For example, the mobile device can include a processor (e.g., a CPU and/or a GPU) for executing computer-readable instructions sorted on memory. In addition, the mobile device can include an internal power source such as a battery, and well-known input components and output components, including, for example, a touch screen, a keypad, speakers, a camera, etc. In addition to the foregoing features, the mobile device can include a communication link (e.g., a wireless transceiver that may include one or more antennas for wirelessly communicating with, for example, other mobile devices, websites, and the sensor devices #1 through #8). Such communication can be performed via, for example, a network (which can include the Internet, public and/or private intranet, a local or extended Wi-Fi network, cell towers, the plain old telephone system (POTS), etc.), direct wireless communication, etc.

The external device 150 and sensor devices 110*a-h* can each include a communication link, which can include a wired connection (e.g. an Ethernet port, cable modem, FireWire cable, Lightning connector, USB port, etc.) or a wireless connection (e.g. including Wi-Fi access point, Bluetooth transceiver, near-field communication (NFC) device, and/or wireless modem or cellular radio utilizing GSM, CDMA, 3G, 4G and/or 5G technologies) for data communication with all manner of remote processing devices via a network connection and/or directly via, for example, a wireless peer-to-peer connection. For example, the communication link can facilitate wireless communication with handheld devices, such as a mobile device (e.g., a smartphone, blood glucose monitor, etc.) either in the proximity of the device or remote therefrom.

In some examples, the external computing devices 180 can take the form of servers, personal computers, tablet computers or other computing devices associated with one of more analytics providers. These external computing devices can collect data recorded by the sensor devices 110*a-h* and/or the external device 150. In some embodiments, such data can be anonymized and aggregated to perform large scale analysis (e.g., using machine learning techniques or other suitable data analysis techniques) to develop and improve athletic performance algorithms using data collected by a large number of sensor devices. Additionally, the external computing devices 180 may be transmit data to the external device 150 and/or the sensor devices 110*a-h*. For example, an updated algorithm for evaluating particular athletic performance developed by the external computing devices (e.g., using machine learning or other techniques) and then provided to the external device 150 and/or the sensor devices 110*a-h* via the network 170 (e.g., as an over the air update) and installed on the appropriate devices.

Figure 3:
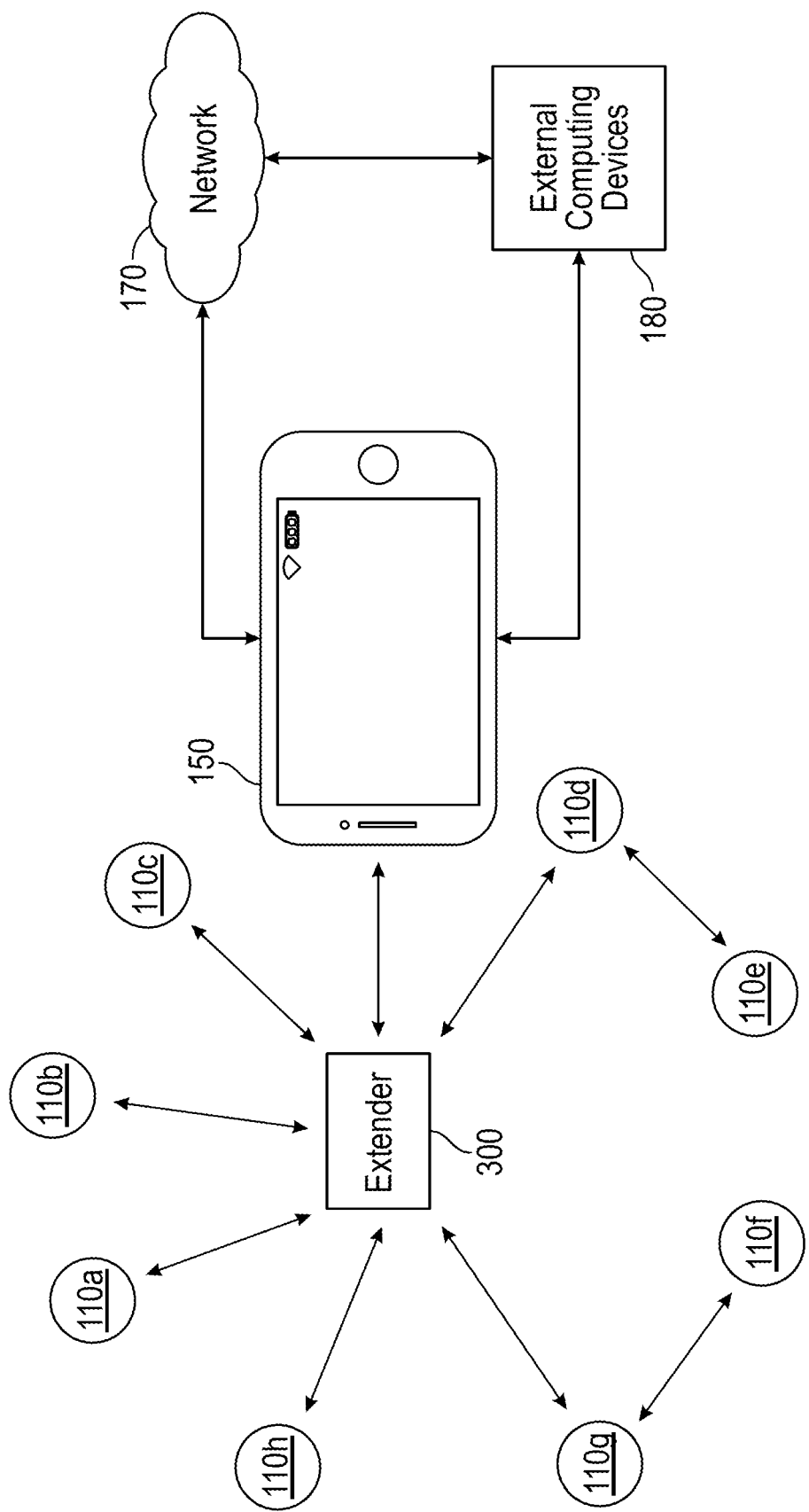
FIG. 3 illustrates another example computing environment suitable for implementing the present technology.

FIG. 3 illustrates another example for the implementation of the system architecture. In contrast to the mesh network among the sensor devices 110*a-h* shown in FIG. 2, the architecture shown in FIG. 3 utilizes a star network configuration, in which a plurality of individual sensor devices 110*a-h* are in communication, either directly or via an intervening sensor device, with an extender 300, which in turn can communicate (e.g., wired or wirelessly) with the external device 150. In some examples, the extender 300 can be a Bluetooth extender device capable of communicating with the sensor devices 110 and/or with the external device 150 over long range, for example greater than about 30 meters, 40 meters, 50 meters, 60 meters, 70 meters, 80 meters, 90 meters, 100 meters, 150 meters, 200 meters, or more. In some examples, and as described in more detail below, the individual sensor devices 110 can be equipped with wireless transceivers that have amplifiers coupled to the antennas so as to boost the range available for transmission of data, e.g., over a Bluetooth communications link.

Example Wearable Sensor Devices

Figure 4:
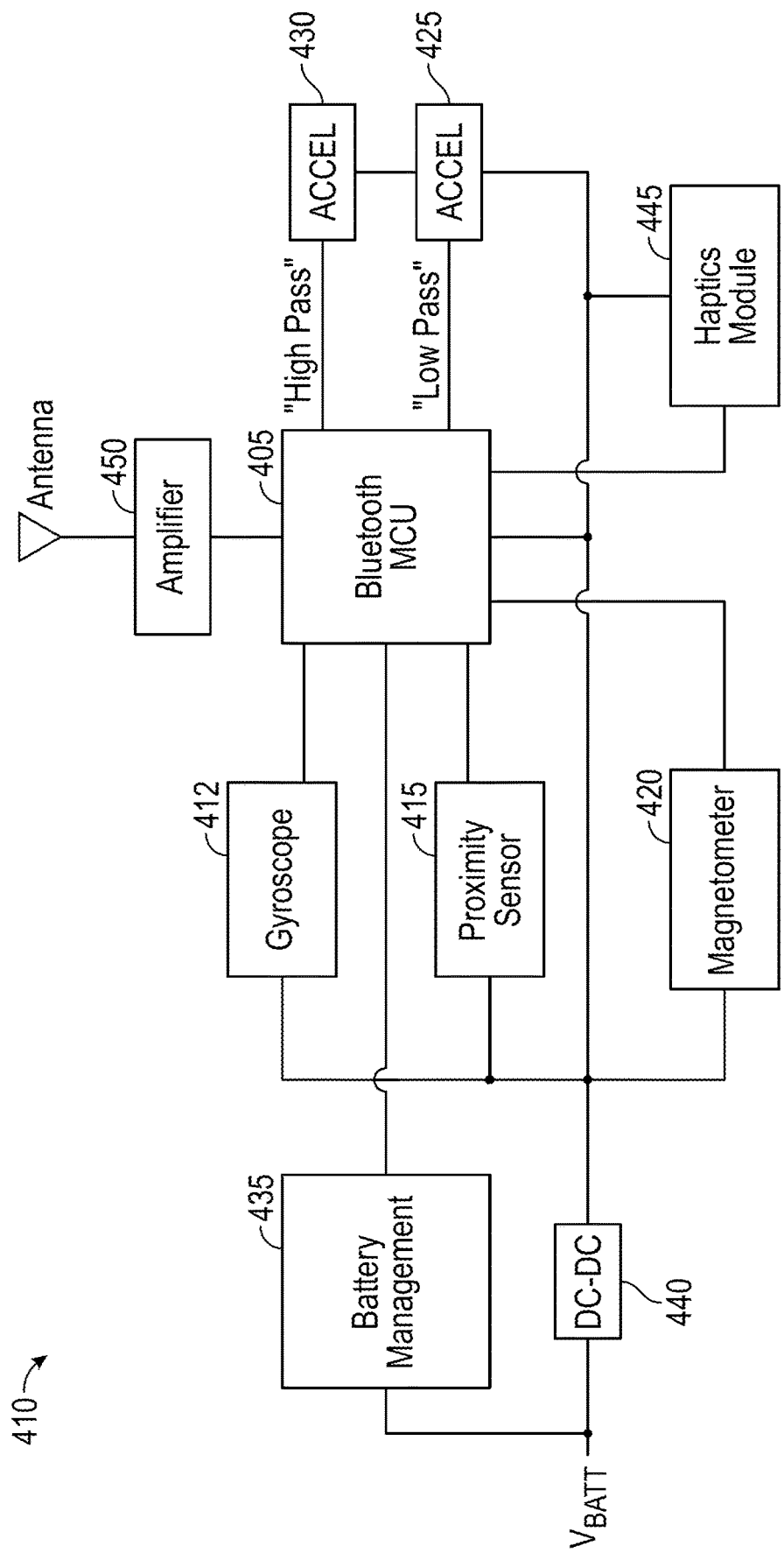
FIG. 4 is a block diagram of a sensor device in accordance with the present technology.
Figure 5A:
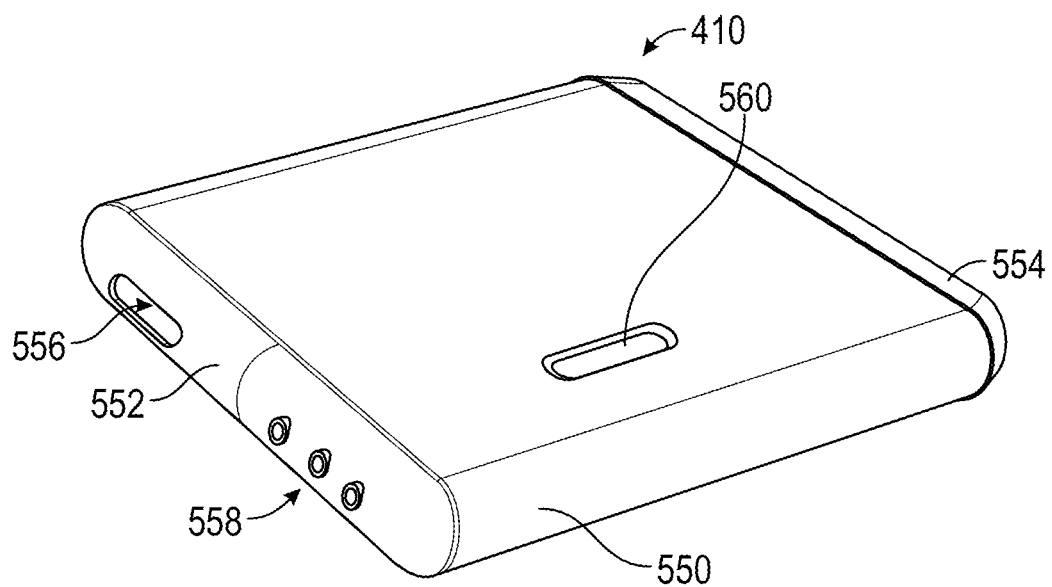
FIG. 5A is a perspective view of an example sensor device in accordance with the present technology.
Figure 5B:
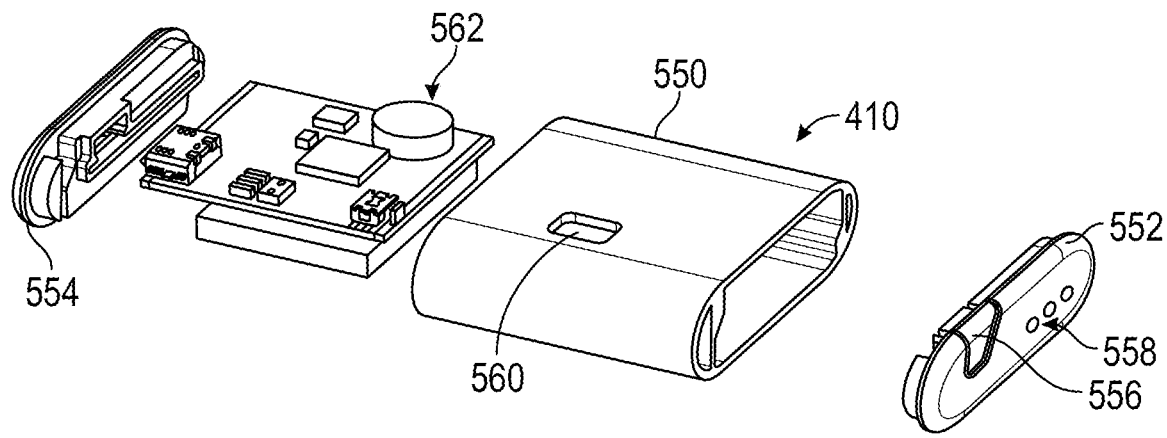
FIG. 5B is a perspective exploded view of the sensor device shown in FIG. 5A.
Figure 5C:
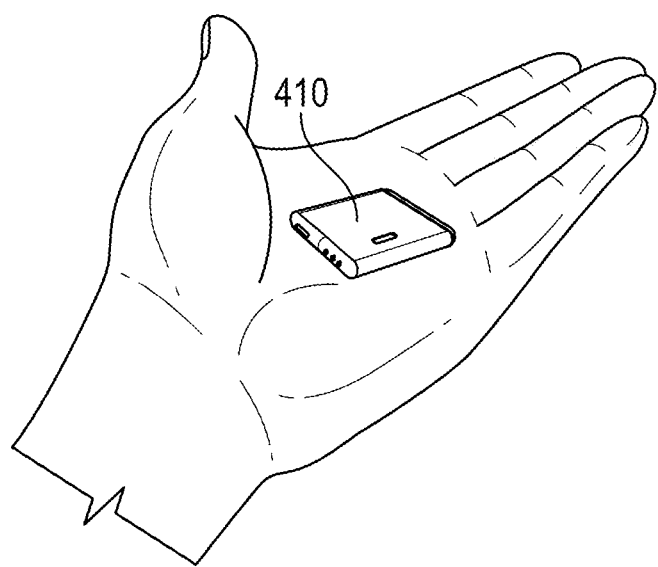
FIG. 5C illustrates the sensor device shown in FIG. 5A in a user's hand.
Figure 5D:
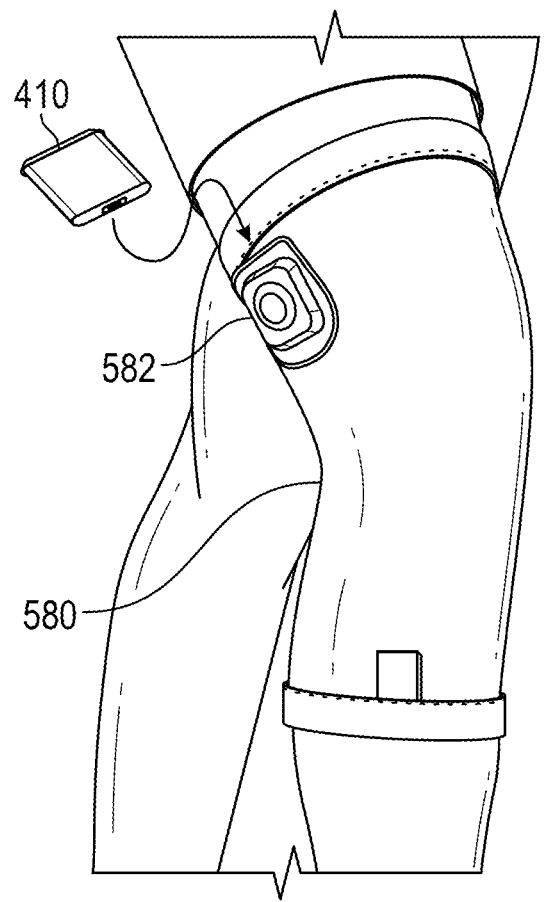
FIG. 5D illustrates the sensor device shown in FIG. 5B incorporated into a wearable garment.
Figure 6:
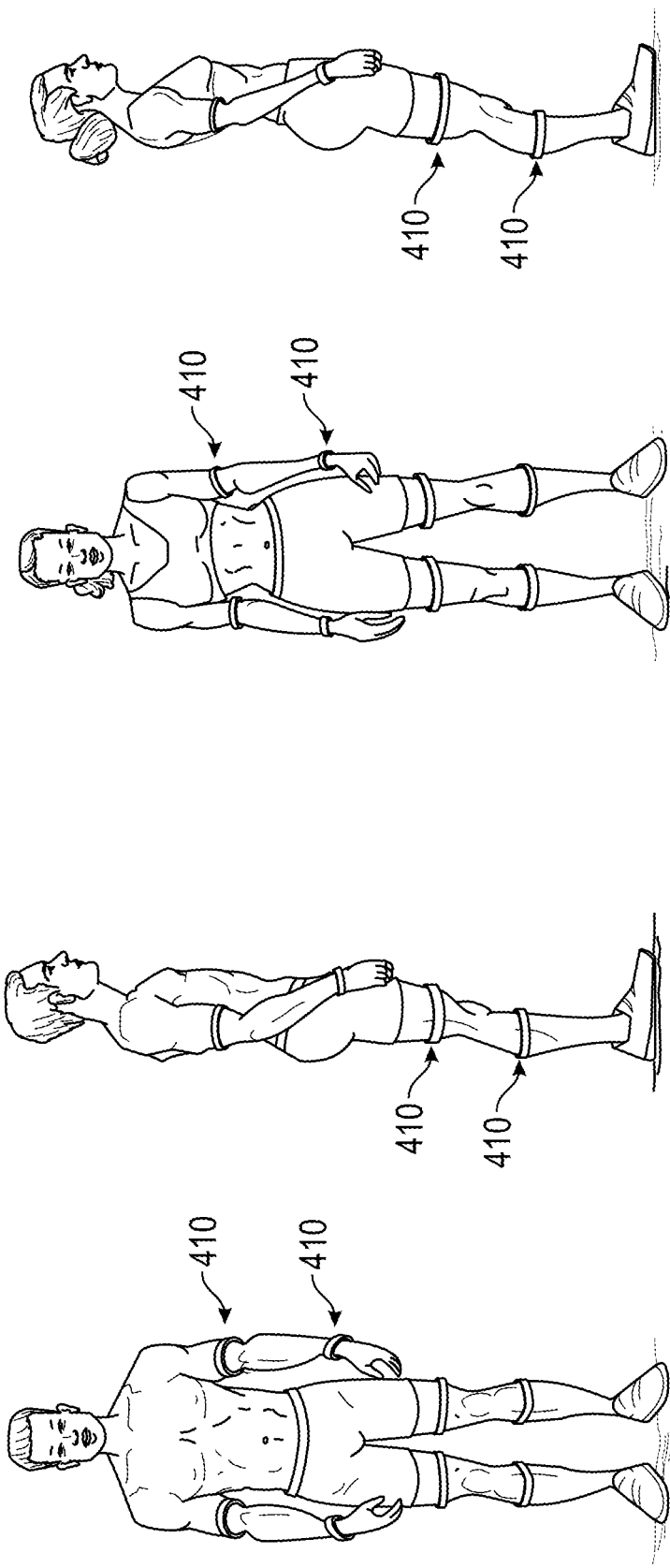
FIG. 6 illustrates example placement locations for sensor devices in accordance with the present technology.

FIGS. 4-6 illustrate example wearable sensor devices and associated uses and placement positions. Some or all of the wearable devices disclosed herein can be worn by a subject (e.g., an athlete) while the subject is active (e.g., while playing a sport). Sensors carried by or otherwise coupled to the wearable device can collect sensor date (e.g., motion, orientation, proximity, etc.). The sensor data can be fed to a computing device (e.g., a microcontroller system or other suitable computing device) and may be transmitted (e.g., wired or wirelessly) to one or more remote computing devices for analysis and evaluation. In some embodiments, a single subject may wear a plurality of sensor devices about the subject's body, and data from some or all of the wearable devices can be used in conjunction to analyze and evaluate the subject's performance. In various embodiments, the wearable devices can be configured to be fastened to the subject's body at various locations—for example the wrists, hands, elbows, shoulders, waist, chest, neck, legs, knees, ankles, or feet. The wearable devices can be incorporated in a housing that can be removably mated with a fastener (e.g., a strap, band, adhesive), incorporated into a garment (e.g., coupled to or carried by a sock, glove, shirt, sleeve, etc.), or otherwise removably or non-removably coupled to the subject's body.

FIG. 4 illustrates a block diagram of an example sensor device 410. Bluetooth Microcontroller Unit (MCU) 405 may receive input signals from one or more local sensors such as, by way of example and not limitation, gyroscope 412, proximity sensor 415, magnetometer 420, accelerometer 425, accelerometer 430 (or any suitable motion sensor) and haptics module 445. Sensor device 410 may further perform optimization functions on the input signals, such as denoising, smoothing, interpolation, extrapolation, etc. using signal processing MCU 405. The sensor device 410 may also include a battery management system 435, which may provide power using a battery and intelligently conserve power as appropriate. The sensor device 410 may further perform optimization functions on the battery input signal, such as regulation and filtering using switching regulator 440. In particular embodiments, sensor device 410 may further include a networking component to transmit data in real time to the gateway device or other peripheral device using, by way of example and not limitation, BLUETOOTH LOW ENERGY or mesh network.

In the illustrated embodiment, the sensor device 410 includes an amplifier 450 coupled to the Bluetooth MCU 405 and also to an antenna. The amplifier 450 and antenna together can be configured to wirelessly communicate with other devices (e.g., other sensor devices, one or more external computing devices, etc.) over a long range, for example greater than about 30 meters, 40 meters, 50 meters, 60 meters, 70 meters, 80 meters, 90 meters, 100 meters, 150 meters, 200 meters, or more.

In operation, the sensor device 410 can be worn by a subject while participating in athletic activities (e.g., playing soccer, track and field, etc.). The sensors, comprised of 9-axis inertial measurement unit or IMU (gyroscope 412, magnetometer 420, and "low pass" accelerometer 425) and stand-alone devices (e.g., proximity sensor 415, and "high pass" accelerometer 430), can collect and transmit data to the MCU 405 via serial interface. The IMU can be used to record rotational and translational movements along x, y, and z axes while the "high pass" accelerometer 430 can be used for vibration detection. Such vibration detection can be used to determine, for example, ball touches (e.g., a soccer player dribbling a ball), striking incidents (e.g., a boxer punching a bag, a baseball hitting a ball), potential concussion risks, etc. The proximity sensor 415 can determine distance between subject and object. The proximity sensor 415 can be, for example, a time-of-flight optical sensor (e.g., LiDAR sensor) or other suitable sensor element configured to determine a distance between the sensor device 410 and an object in the surrounding environment, such as other athletes, equipment, reference objects, etc. In various embodiments, any suitable type of proximity sensor can be used.

In some embodiments, sensor fusion technology is used to combine data from the aforementioned sensors to create a more accurate representation of the subject environment, thereby circumventing the performance limitations of the individual sensors, respectively. In particular embodiments, a sensor fusion implementation may use a gyroscope, accelerometer and/or magnetometer, by way of example and not limitation, to determine subject orientation. In a particular embodiment, proximity sensor, by way of example and not limitation, replaces the IMU accelerometer for positional tracking. In an additional embodiment haptics module 445 may provide haptic feedback and/or vibration alerts to the subject as notification of subject's level of performance during the respective athletic activities.

FIGS. 5A-5D illustrate various views of an example sensor device 410. As shown in FIGS. 5A and 5B, the sensor device 410 can include a housing 550 that includes first and second end portions 552 and 554 configured to mate on opposing sides of the housing 550. The housing can be substantially water-impermeable or water-resistant, and can be made of a durable material such as rigid plastics, ceramics, metals (e.g., titanium, aluminum, etc.). In some examples, the housing can be coated with an elastomeric material to enhance grip or improve the look and/or feel of the sensor device 410.

The sensor device 410 can include a power button 556, which can be accessible through or integrated into the housing 550. The power button can be depressible to transition the device 410 into a low-power, high-power, or no-power state. In some examples, the device 410 can enter a low-power sleep state after a predetermined period of time has passed in which no motion is detected, and depressing the power button 556 can cause the device 410 to wake up.

The sensor device 410 can further include one or more lights 558 disposed on or visible through the housing 550. In various examples, the lights 558 can be configured to indicate to a user a power status, battery level, wireless connectivity status, or performance-based feedback to the user. As shown in FIGS. 5A and 5B, the housing 550 can include an aperture 560 or window, which can be an open space or can be filled with a transparent or translucent material configured to let optical signals pass therethrough. In operation, a proximity sensor (e.g., a LiDAR sensor) can be disposed adjacent the aperture 560 and be configured to emit and receive optical signals (or other suitable sensor signals) through the aperture 560 for detection of objects in proximity to the sensor device 410. In various examples, the sensor device 410 can include a plurality of such apertures 560 disposed about the device 410, for example on opposing or alternative sides of the housing 550. As seen in FIG. 5B, an electronics assembly 562 can be received within the housing 562. The electronics assembly 562 can include a plurality of components coupled together, for example mounted onto a printed circuit board or other suitable substrate. Such components can include, for example, sensor elements, wireless communications components, battery or power components, etc. In some embodiments, the sensor device 410 can be rechargeable, for example via wireless charging (e.g., inductive charging) or wired charging (e.g., via a wired charging connector such as a micro-USB port or other suitable connection).

As shown in FIG. 5C, the wearable sensor device 410 can be small enough to fit in the palm of an athlete's hand, and as shown in FIG. 5D can be removably (or non-removably) incorporated into a garment 580 such as a sock, sleeve, hat, glove, brace, shirt, shorts, etc. In the illustrated example, the garment 580 includes a pocket 582 or other suitable receptacle configured to receive the sensor device 410 therein. In some embodiments, the pocket 582 or other receptacle can include a window, aperture, or other feature configured to permit the proximity sensor of the sensor device 410 to operate therethrough to detect nearby objects or people.

FIG. 6 illustrates example locations for sensor device(s) 410. As illustrated, sensor devices 410 can be coupled to, by way of example and not limitation, a subject's arms (e.g., biceps, elbow, wrist, or other suitable location) and/or legs (e.g., thighs, knees, shins, or other suitable location). In operation, data collected via sensors carried by the wearable devices can be analyzed in real-time, near real-time, or at a later time to evaluate the subject's athletic performance.

Example Footwear-Carried Sensor Devices

Figure 7:
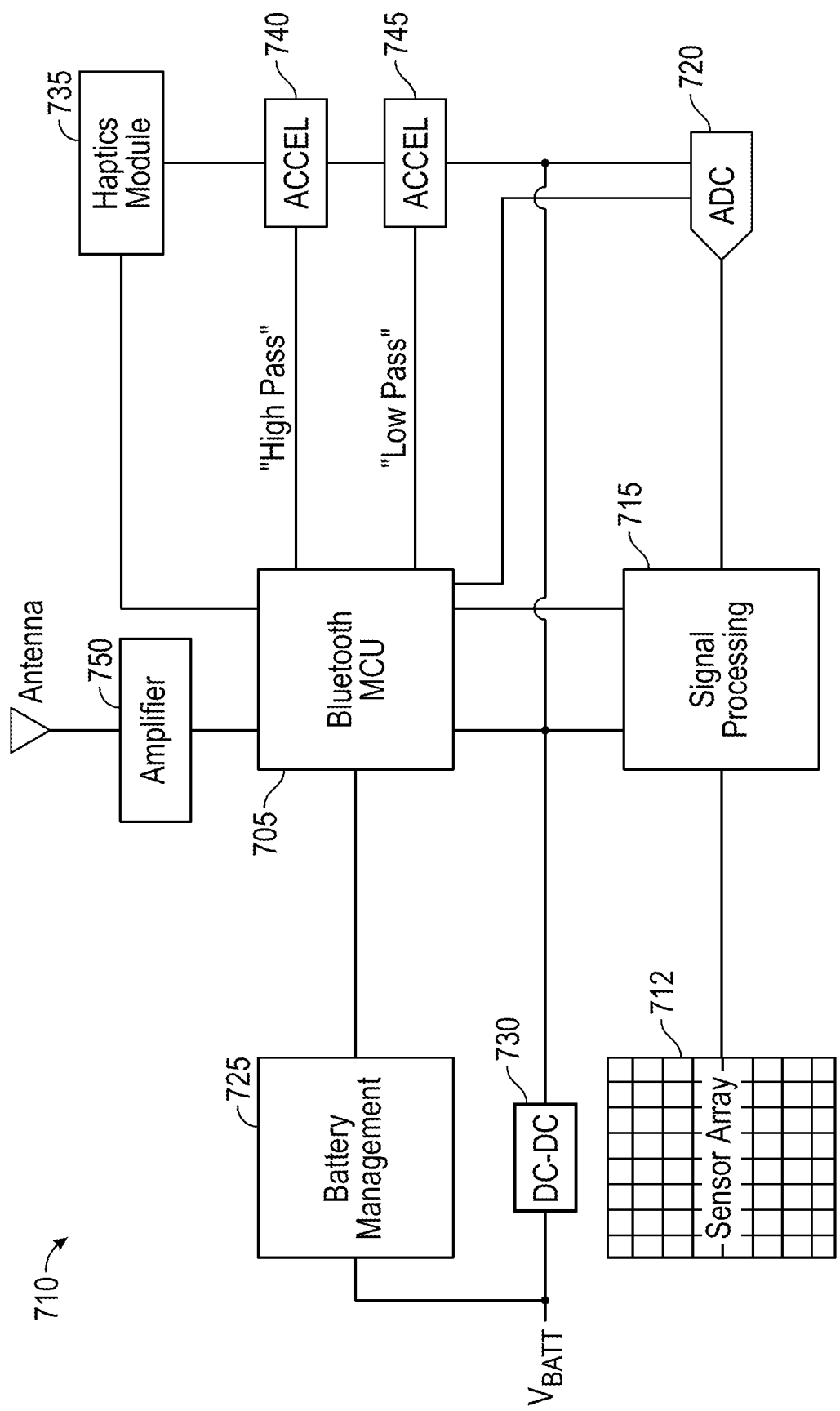
FIG. 7 is a block diagram of another example sensor device in accordance with the present technology.

FIG. 7 illustrates a block diagram of an example sensor device 710. Bluetooth Microcontroller Unit (MCU) 705 may receive input signals from one or more local sensors such as, by way of example and not limitation, pressure sensor 712. The pressure sensor 712 can be, for example, a sensor array comprised of force sensing resistors to transduce force to voltage and/or current signals. In various embodiments, any suitable pressure sensor can be used. In particular embodiments, output signals from pressure sensor 712 may be pre-processed using signal processing unit 715 and analog-to-digital converter 720. In particular embodiments, signal processing unit 715 may amplify or attenuate its input signal. Wearable device 710 may further perform optimization functions on the input signals, such as denoising, smoothing, interpolation, extrapolation, etc. using signal processing MCU 705. Wearable device 710 may also include a battery management system 725, which may provide power using a battery and intelligently conserve power as appropriate. Wearable device 700 may additionally include haptics module 735, which may provide haptic feedback and/or vibration alerts to the subject. Wearable device 700 may further perform optimization functions on the battery input signal, such as regulation and filtering using switching regulator 730. In particular embodiments, wearable device 700 may further include a networking component to transmit data in real time to the gateway device or other peripheral device using, by way of example and not limitation, BLUETOOTH LOW ENERGY or mesh network.

In the illustrated embodiment, the sensor device 710 includes an amplifier 750 coupled to the Bluetooth MCU 705 and also to an antenna. The amplifier 750 and antenna together can be configured to wirelessly communicate with other devices (e.g., other sensor devices, one or more external computing devices, etc.) over a long range, for example, greater than about 30 meters, 40 meters, 50 meters, 60 meters, 70 meters, 80 meters, 90 meters, 100 meters, 150 meters, 200 meters, or more.

Pressure sensor 712 measures the force applied to the sensor by modulating its resistance based on the applied force. Based on data collected from the combination of sensors (e.g., IMU, proximity, accelerometer, and pressure), the following metrics can be accurately determined: position, orientation, speed, acceleration, vibration, and force. In an additional embodiment haptics module 735 may provide haptic feedback and/or vibration alerts to the subject as notification of subject's level of performance during the respective athletic activities.

Figure 8:
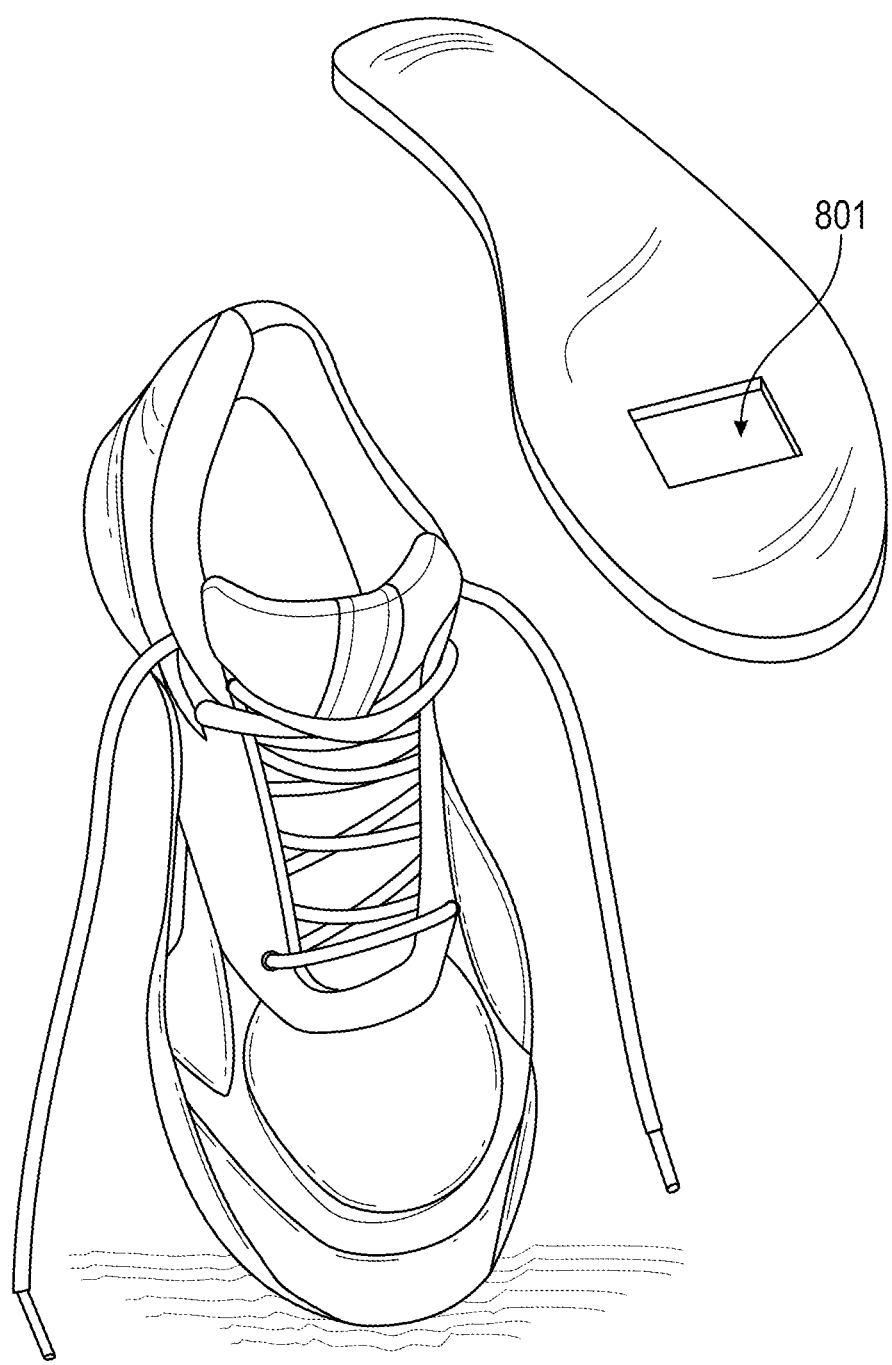
FIG. 8 illustrates another example sensor location for a sensor device in accordance with the present technology.

FIG. 8 illustrates an example sensor device 710 location. As illustrated, the sensor device 710 can be incorporated into a shoe, for example, by being disposed within a recess in the sole of the shoe. In operation, the sensor device can sense (e.g., via pressure sensor 712 or in conjunction with accelerometers or proximity sensors of sensor devices 110, 410) the subject's gait, running pace, the forces experienced by the user's foot during jumping or running, or other athletic performance parameters.

Example Equipment-Mounted Sensor Devices

FIGS. 9-13 illustrate example sensor devices that may be mounted to sports equipment or other objects and are intended to measure sports performance without being carried by the athlete's body, as well as exemplary mounting configurations and associated processes that may be performed using such sensors. For example, the sensor devices can include proximity sensors able to detect the presence of a soccer ball nearing a goal. The sensor data can be fed to a computing device (e.g., a microcontroller system or other suitable computing device) and may be transmitted (e.g., wired or wirelessly) to one or more remote computing devices for analysis and evaluation.

Figure 9:
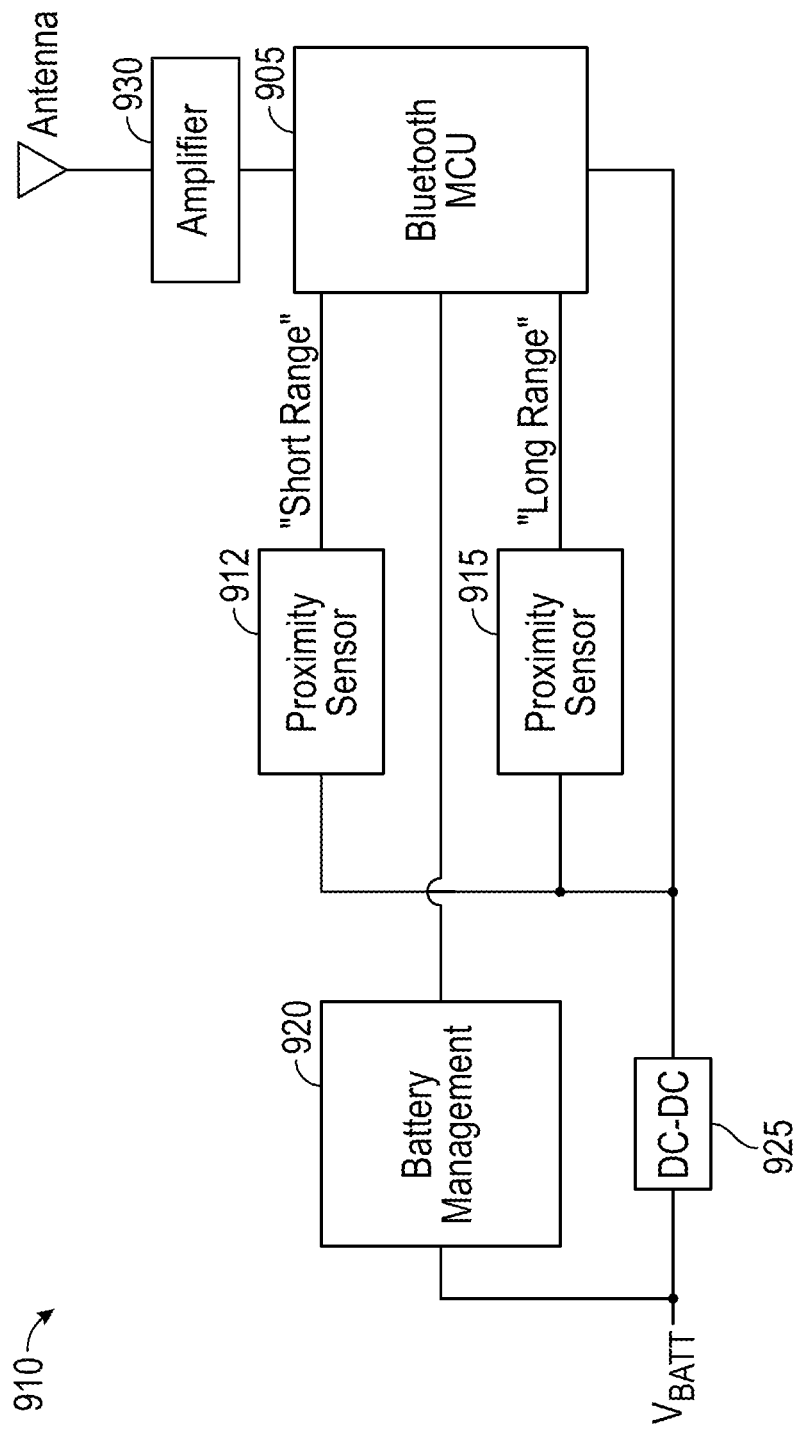
FIG. 9 is a block diagram of another example sensor device in accordance with the present technology.

FIG. 9 illustrates a block diagram of an example sensor device 910. Bluetooth Microcontroller Unit (MCU) 905 may receive input signals from one or more local sensors such as, by way of example and not limitation, proximity sensor 912 and proximity sensor 915. In some embodiments, the proximity sensor 912 can be a "short range" proximity sensor, for example, being configured to detect the presence of a nearby object or surface within approximately 1 inch, and the proximity sensor 915 can be a "long range" proximity sensor, for example being configured to detect the presence of an object or surface within approximately 12 feet. Sensor device 910 may further perform optimization functions on the input signals, such as denoising, smoothing, interpolation, extrapolation, etc. using signal processing MCU 905. Sensor device 910 may also include a battery management system 920, which may provide power using a battery and intelligently conserve power as appropriate. Sensor device 910 may further perform optimization functions on the battery input signal, such as regulation and filtering using a switching regulator 925. In particular embodiments, sensor device 910 may further include a networking component to transmit data in real time to the gateway device or other peripheral device using, by way of example and not limitation, BLUETOOTH LOW ENERGY or mesh network.

In the illustrated embodiment, the sensor device 910 includes an amplifier 930 coupled to the Bluetooth MCU 905 and also to an antenna. The amplifier 930 and antenna together can be configured to wirelessly communicate with other devices (e.g., other sensor devices, one or more external computing devices, etc.) over a long range, for example greater than about 30 meters, 40 meters, 50 meters, 60 meters, 70 meters, 80 meters, 90 meters, 100 meters, 150 meters, 200 meters, or more.

Proximity sensors 912 and 915, by way of example and not limitation, can be used to divide a goal into twelve smaller regions of interest (ROI) to determine the location of the ball as it crosses the goal threshold. For example, a soccer goal, 8 feet high by 24 feet wide, would have ROIs (2.67 feet high by 6 feet wide). A goal detection, and location, can then be determined from the placement of a ball within a respective ROI.

Figure 10B:
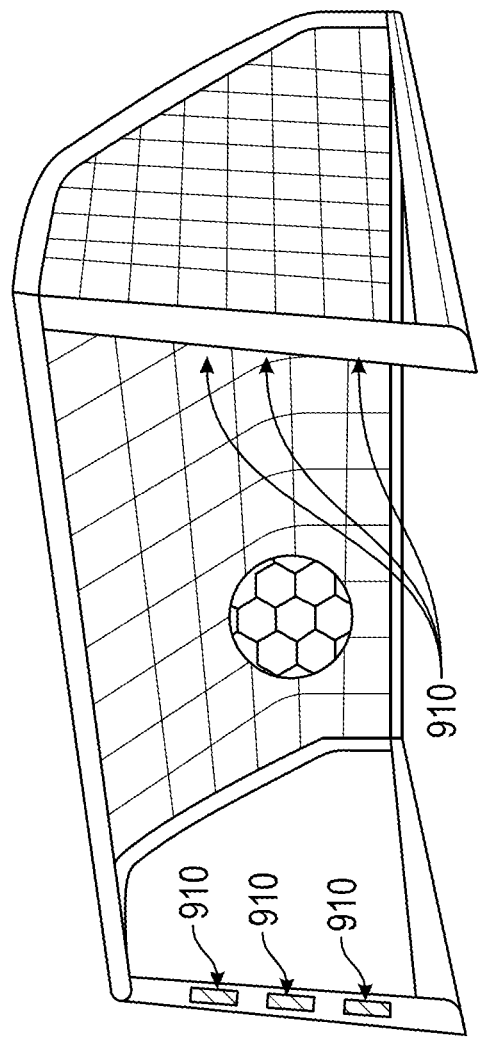
FIG. 10B illustrates example placement locations of sensor devices about a soccer goal in accordance with the present technology.
Figure 10A:
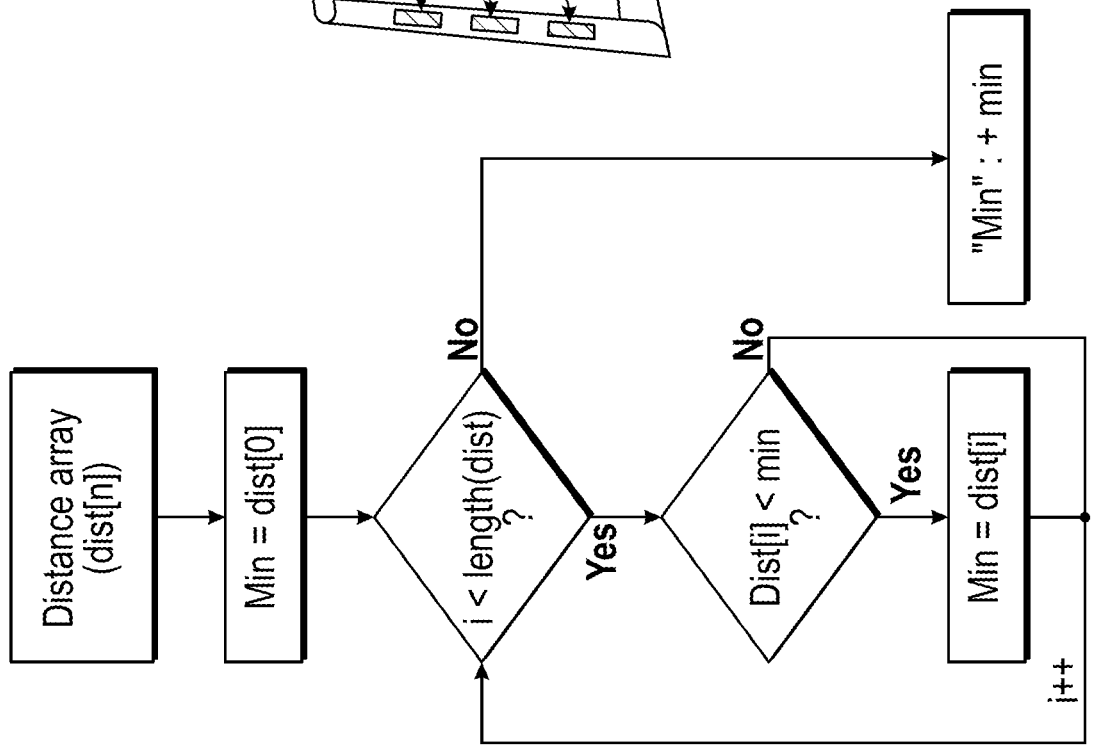
FIG. 10A is an example flow diagram of a process for generating a heat-map of ball locations with respect to a soccer goal using sensor devices in accordance with the present technology.

FIG. 10A is an example of a goal heat-map generation algorithm using sensor devices 910. FIG. 10B illustrates an example configuration of sensor devices 910 disposed about a soccer goal. As illustrated by way of example and not limitation, the sensor devices can be disposed about a soccer goal, with the proximity sensors configured to detect the presence of the ball and/or, in conjunction with sensor device 410, any players and their respective positions. In some embodiments, the sensors can detect when the ball has crossed the goal line. For example, proximity sensors disposed about goal can be configured to divide goal dimensions into 12 regions. Ball positions within the regions may be determined thereby determining the location of the shot. Heat maps may be generated from which placement accuracy metric may be derived. In particular embodiments, proximity sensors and wearables, by way of example and not limitation, can be combined to reconstruct a shooting sequence animation obviating the need for video analysis.

Figure 11:
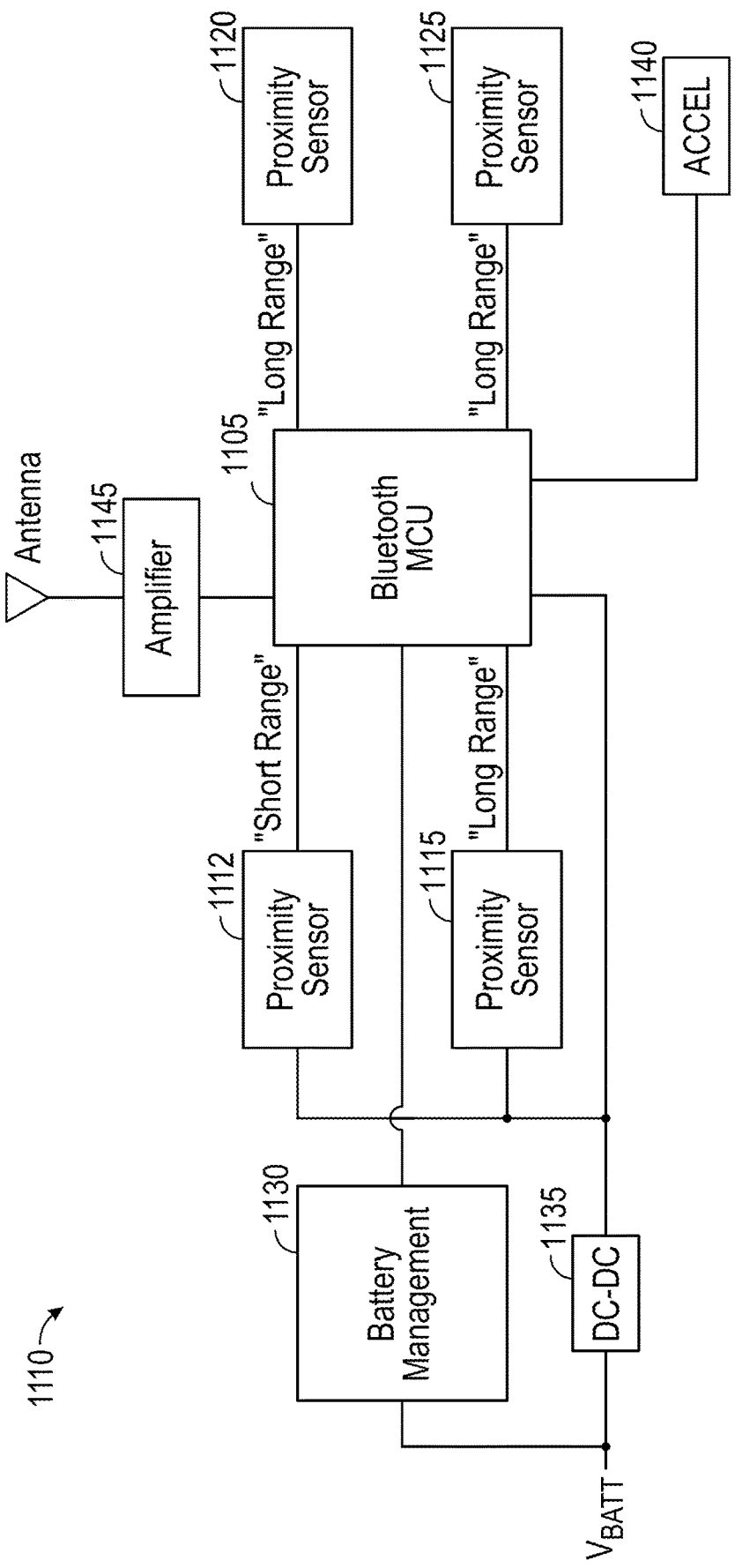
FIG. 11 is a block diagram of another example sensor device in accordance with the present technology.

The particular configuration of the sensor device(s) can depend, at least in part, on the sport or other athletic context. For example, sensors configured for use in evaluating athletic performance of soccer players may differ from those used in evaluating athletic performance of basketball players. One example of a suitable sensor device for use in the context of basketball is shown in FIG. 11, which shows a block diagram of another example sensor device 1100. Bluetooth Microcontroller Unit (MCU) 1105 may receive input signals from one or more local sensors such as, by way of example and not limitation, proximity sensor 1112, proximity sensor 1115, proximity sensor 1120, proximity sensor 1125 and accelerometer 1140. Proximity sensor 1112 determines "short range" distances up to approximately 3 feet. Proximity sensors 1115, 1120 and 1125 determine "long range" distances of greater than 10 feet, for example up to approximately 39 feet. Sensor device 1110 divides the training area into circular regions of interest (ROI) spanning 180 degrees with the sensor device at the center of the intimated circle. Overlap in ranges increases measurement accuracy. Accelerometer 1140 detects vibration/shock events. The sensor device 1110 may further perform optimization functions on the input signals, such as denoising, smoothing, interpolation, extrapolation, etc. using signal processing MCU 1105. The sensor device 1110 may also include a battery management system 1130, which may provide power using a battery and intelligently conserve power as appropriate. The sensor device 1110 may further perform optimization functions on the battery input signal, such as regulation and filtering using switching regulator 1135. In particular embodiments, the sensor device 1110 may further include a networking component to transmit data in real time to the gateway device or other peripheral device using, by way of example and not limitation, BLUETOOTH LOW ENERGY or mesh network.

In the illustrated embodiment, the sensor device 1110 includes an amplifier 1145 coupled to the Bluetooth MCU 1105 and also to an antenna. The amplifier 1145 and antenna together can be configured to wirelessly communicate with other devices (e.g., other sensor devices, one or more external computing devices, etc.) over a long range, for example greater than about 30 meters, 40 meters, 50 meters, 60 meters, 70 meters, 80 meters, 90 meters, 100 meters, 150 meters, 200 meters, or more.

Figure 12:
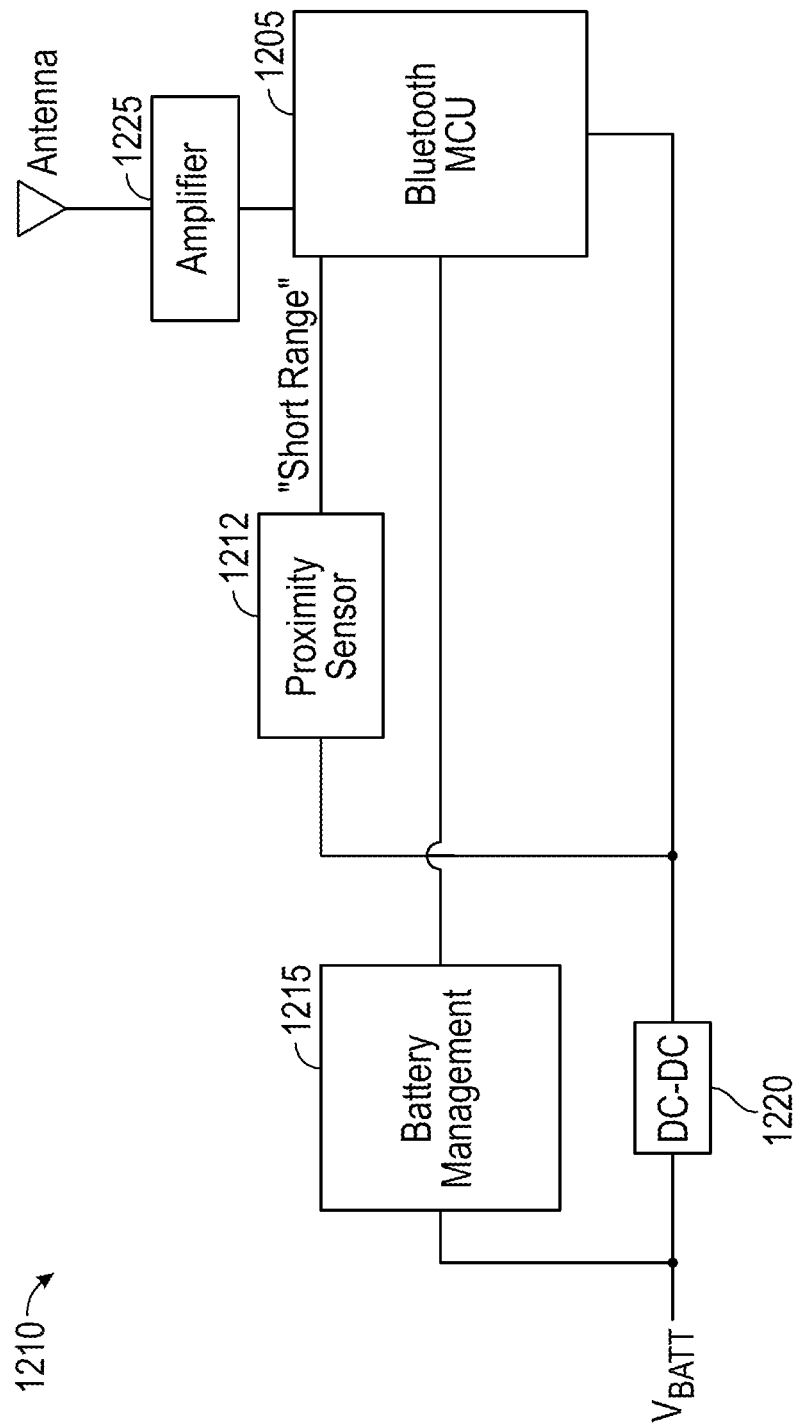
FIG. 12 is a block diagram of another example sensor device in accordance with the present technology.

FIG. 12 illustrates a block diagram of another example sensor device 1210. In some embodiments, the sensor device 1210 can be configured for use while mounted to a basketball backboard. Bluetooth Microcontroller Unit (MCU) 1205 may receive input signals from one or more local sensors such as, by way of example and not limitation, proximity sensor 1212. In the illustrated example, the sensor device 1210 includes a single "short range" proximity sensor 1212, though in alternative embodiments additional sensors can be incorporated. The sensor device 1210 may further perform optimization functions on the input signals, such as denoising, smoothing, interpolation, extrapolation, etc. using signal processing MCU 1205. The sensor device 1210 may also include a battery management system 1215, which may provide power using a battery and intelligently conserve power as appropriate. The sensor device 1210 may further perform optimization functions on the battery input signal, such as regulation and filtering using switching regulator 1220. In particular embodiments, the sensor device 1210 may further include a networking component to transmit data in real time to the gateway device or other peripheral device using, by way of example and not limitation, BLUETOOTH LOW ENERGY or mesh network. The device 1210 can also include an amplifier 1225 configured to enable long-range wireless communication with other devices (e.g., other sensor devices, one or more external computing devices, etc.), for example greater than about 30 meters, 40 meters, 50 meters, 60 meters, 70 meters, 80 meters, 90 meters, 100 meters, 150 meters, 200 meters, or more.

In operation, the proximity sensors 1112, 1115, 1120 and 1125 (FIG. 11), as well as proximity sensor 1212 (FIG. 12) can be used to evaluate athletic performance of a basketball player or players. The sensor device 1110, by way of example and not limitation, can divide a basketball halfcourt into smaller regions of interest (ROI), spanning 180 degrees, to determine the athlete's location relative to the sensor device 1110. The combination of data from sensor devices disclosed herein (e.g., 110, 410, 710 and 500, by way of example and not limitation, can be used to generate a 3D animation of an athlete's dribbling and shooting training sessions. The devices, in conjunction, may further provide metrics pertaining to the athlete's shooting statistics (e.g., field goal attempts, field goal percentage, and points scored including 3-point goals). In particular embodiments, the sensor device 1110 determines if the shot hit the backboard and/or rim before going through the hoop via vibration and/or shock detection accelerometer 1140.

Figure 13B:
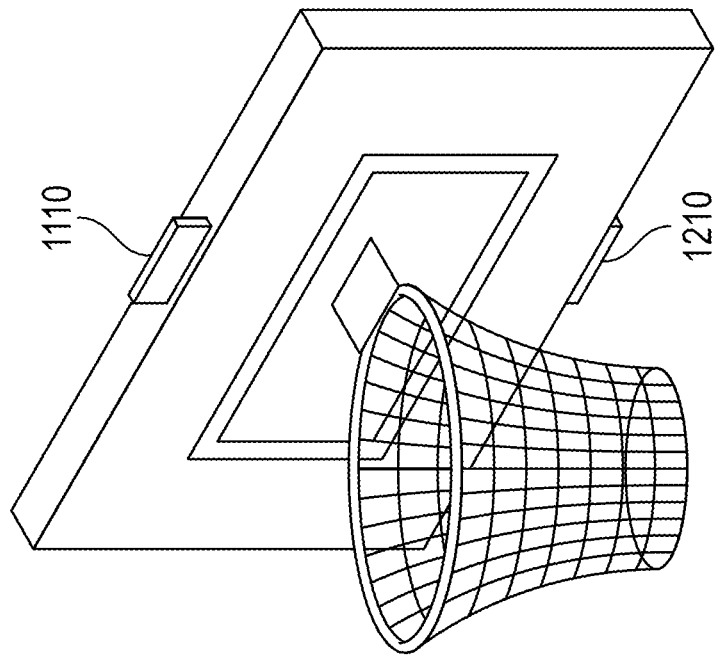
FIG. 13B illustrates example placement locations of sensor devices about a basketball backboard and rim goal in accordance with the present technology.
Figure 13A:
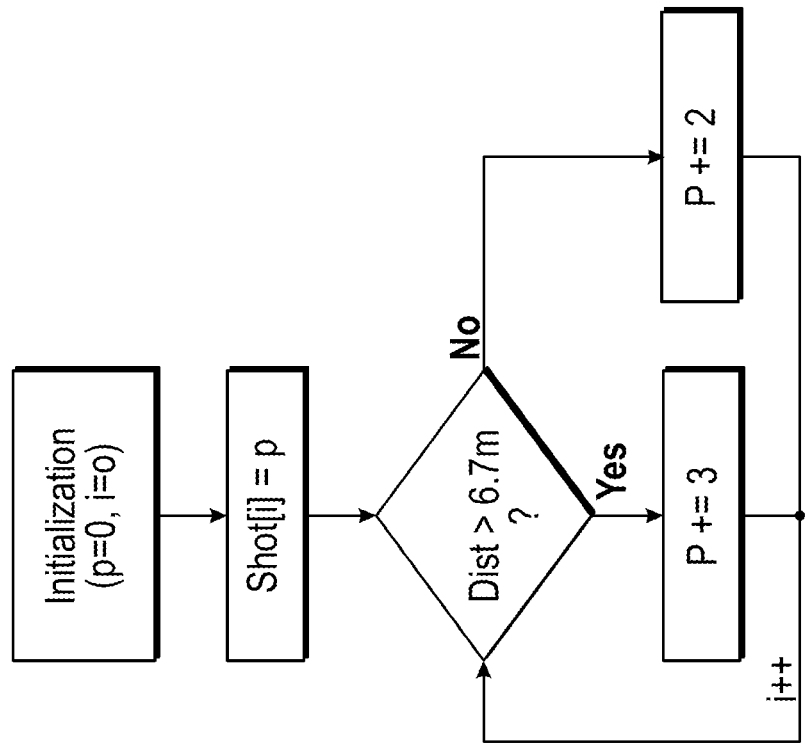
FIG. 13A is an example flow diagram of a process for tracking basketball shots using sensor devices in accordance with the present technology.

FIG. 13A illustrates an example process for detecting a basketball shot using sensors 1110 and 1210. FIG. 13B illustrates example locations for mounting sensor devices 1110 and 1210 with respect to a basketball hoop and backboard. As illustrated by way of example and not limitation, the sensor devices can be disposed about a basketball hoop and backboard, with the proximity sensors configured to detect the presence of the ball and/or athlete(s). In some embodiments, the sensors can be configured to detect when the ball has touched the backboard and/or rim and/or when the ball has passed through the hoop. For example, proximity sensors attached above and below the basketball backboard can track location of shooter and vertical direction of the ball to determine whether the shooter has scored a basket. Furthermore, 2 or 3 points are associated with the scored basket based on the distance of the shooter from the backboard. In particular embodiments, proximity sensors and wearables, by way of example and not limitation, can be combined to reconstruct a shooting sequence animation obviating the need for video analysis.

The sensor device 1210, by way of example and not limitation, determines the success of a goal attempt. The combination of data from additional sensor devices (e.g., 110, 410, 710, 910, and 1110) can be used to provide a 3D animation of an athlete's dribbling and shooting training sessions. The devices, in conjunction, may further provide metrics pertaining to the athlete's shooting statistics (e.g., field goal attempts, field goal percentage, and points scored including 3-point goals) and field goal dynamics (e.g., nothing but net, backboard and/or rim).

III. Examples

Various exemplary use cases are described below. As will be appreciated by one of skill in the art, there are numerous other possible uses and applications of the sensor technology disclosed herein. Additionally, various modifications may be made to the example use cases below, as desired to achieve the intended outcome.

Example 1: Measure Athlete's Vertical Leap

Summary: An athlete jumps vertically. Determine the maximum displacement, the athlete's vertical leap.

Actors: Athlete, target

Preconditions: Wearable sensors are in place. Active Bluetooth Network. Target is in place.

Description
1. Determine position of sensors with athlete at standing rest (gyroscope, accelerometer, magnetometer)
2. Determine position of sensors with athlete at peak vertical displacement (gyroscope, accelerometer, magnetometer)
3. Determine the difference between steps 1 and 2 (gyroscope, accelerometer, magnetometer)
4. Provide performance-related haptic and/or vibrational feedback to athlete (haptics module)
5. Provide contextual 3D motion-tracking animation showing athlete jumping
6. Provide vertical leap performance summary. The use case terminates at this point.

Example 2: Provide Contextual Metrics Pertaining to Shooting Accuracy of Basketball Player Summary: A basketball player is in shooting practice. Map out the ball trajectory and location as the player shoots the ball into the goal. Provide the following metrics—number of points, shooting percentage, shooting speed, shooting mechanics, Actors: Basketball player, ball, goal Preconditions: Wearable sensors and proximity sensors are in place. Active Bluetooth Network. Basketball player is possession of the ball during the activity.

Description
1. Determine position of player with the ball (proximity sensor)
2. Determine when player shoots the ball (gyroscope, accelerometer, magnetometer)
3. Determine time and location when the ball enters the goal (proximity sensor)
4. Determine if made shot is 2 points or 3 points
5. Provide performance-related haptic and/or vibrational feedback to basketball player (haptics module)
6. Provide contextual 3D motion-tracking animation showing basketball player shooting the ball into the goal
7. Provide shooting performance summary, technique, points, and accuracy. The use case terminates at this point.

Example 3: Provide Contextual Metrics Pertaining to Ball Mastery of a Soccer Player Dribbling Through Cone Formations Summary: A soccer player possesses the ball. Map out the cone formation as player traverses the course. Determine ball mastery metrics—number of touches, ball proximity, touch rate, change of speed, change of direction, technique, efficiency, creativity.

Actors: Soccer player, ball, cones

Preconditions: Wearable sensors are in place. Active Bluetooth Network. Cone formation complete. Soccer player is possession of the ball during the activity.

Description
1. Determine position of the ball (pressure sensor)
2. Determine location of the cones (proximity sensor)
3. Determine rotational and translational movements of player with the ball (gyroscope, accelerometer, magnetometer)
4. Provide performance-related haptic and/or vibrational feedback to soccer player (haptics module)
5. Provide contextual 3D motion-tracking animation showing soccer player dribbling through cone formation.
6. Provide ball mastery performance summary, technique.

Example 4: Provide Contextual Metrics Pertaining to Shooting Accuracy of a Soccer Player Summary: A soccer player is in shooting practice. Map out the ball trajectory and location as the player shoots into the goal.

Actors: Soccer player, ball, goal

Preconditions: Wearable sensors and proximity sensors are in place. Active Bluetooth Network. Soccer player is possession of the ball during the activity.

Description
1. Determine position of the ball (pressure sensor)
2. Determine location of player with the ball (proximity sensor)
3. Determine when player kicks the ball (gyroscope, accelerometer, magnetometer)
4. Determine time and location when the ball enters the goal (proximity sensor)
5. Provide performance-related haptic and/or vibrational feedback to soccer player (haptics module)
6. Provide contextual 3D motion-tracking animation showing soccer player kicking the ball into the goal
7. Provide shooting performance summary, technique, and accuracy

Example 5: Provide Contextual Metrics Pertaining to Running Technique of a Track and Field Sprinter Summary: A sprinter is in training. Analyze the running mechanics. Provide the following analysis—gait analysis, cadence turnover, acceleration, start technique, speed.

Actors: Sprinter

Preconditions: Wearable sensors are in place. Active Bluetooth Network. Sprinter is ready.

Description
1. Determine sprinter start technique (pressure sensor)
2. Biomechanical analysis (gyroscope, accelerometer, magnetometer)
3. Provide performance-related haptic or vibrational feedback to sprinter (haptics module)
4. Provide contextual 3D motion-tracking animation showing sprinter running
5. Provide performance summary, gait analysis, cadence, turnover, acceleration, technique and speed.

Example 6: Provide Contextual Metrics Pertaining to Patient Remote Physical Therapy and Rehabilitation Summary: A patient is in a physical therapy session from home. Perform a biomechanical analysis and share the results with a remote care team. Provide the following analysis—gait analysis, force analysis.

Actors: Patient

Preconditions: Wearable sensors are in place. Active Bluetooth Network. Internet access. Patient is ready.

Description
1. Biomechanical analysis (gyroscope, accelerometer, magnetometer, pressure sensor)
2. Provide performance-related haptic or vibrational feedback to patient (haptics module)
3. Provide contextual 3D motion-tracking animation showing patient doing therapy exercises
4. Provide performance summary, gait analysis, force analysis
5. Upload animation and summary to one or more remote computing devices.

Example 7: Provide Contextual Metrics Pertaining to Hand Speed and Punching Power of a Boxer Summary: A boxer is in a heavy bag workout. Determine the hand speed and punching power as the boxer strikes the heavy bag.

Actors: Boxer, gloves, heavy bag

Preconditions: Wearable sensors are in place. Active Bluetooth Network. Boxer is wearing gloves during the activity.

Description
1. Determine location of the heavy bag (proximity sensor)
2. Determine movement of the boxer (gyroscope, accelerometer, magnetometer)
3. Determine when boxer hits the heavy bag and power of the punch (accelerometer)
4. Determine speed of the punch (gyroscope, accelerometer, magnetometer)
5. Provide performance-related haptic and/or vibrational feedback to boxer (haptics module)
6. Provide contextual 3D motion-tracking animation showing boxer punching the heavy bag
7. Provide punching performance summary, power, technique, and speed.

Example 8: Provide Contextual Metrics Pertaining to Kicking Speed and Power of a Martial Artist Summary: A martial artist is in heavy bag workout. Determine the kicking speed and power as the martial artist strikes the heavy bag.

Actors: Martial artist, gloves, training shoes, heavy bag

Preconditions: Wearable sensors are in place. Active Bluetooth Network. Martial artist is wearing gloves and training shoes during the activity.

Description
1. Determine location of the heavy bag (proximity sensor)
2. Determine movement of the martial artist (gyroscope, accelerometer, magnetometer)
3. Determine when martial artist hits the heavy bag and power of the kick (accelerometer)
4. Determine speed of the kick (gyroscope, accelerometer, magnetometer)
5. Provide performance-related haptic and/or vibrational feedback to boxer (haptics module)
6. Provide contextual 3D motion-tracking animation showing martial artist kicking the bag
7. Provide kicking performance summary, power, technique and speed. The use case terminates at this point.

Example 9: Provide Contextual Metrics Pertaining to Swing Analysis, Bat Speed and Hitting Power of a Baseball Batter Summary: A baseball batter is in batting practice. Perform a biomechanical analysis and provide force analysis and metrics for power, swing speed and technique Actors: Batter, bat, pitcher (person or machine), ball Preconditions: Wearable sensors are in place. Active Bluetooth Network. Batter is using a bat during the activity.

Description
1. Biomechanical analysis (gyroscope, accelerometer, magnetometer, pressure sensor)
2. Determine power of the swing as batter makes contact with the ball and (accelerometer)
3. Determine speed of the swing (gyroscope, accelerometer, magnetometer)
4. Determine location of the ball (proximity sensor)
5. Provide performance-related haptic and/or vibrational feedback to batter (haptics module)
6. Provide contextual 3D motion-tracking animation showing batter's swing and location of the ball
7. Provide batting performance summary, power, technique, and speed.

Example 10: Provide Contextual Metrics Pertaining to Swing Analysis, Club Speed and Hitting Power of a Golfer Summary: A golfer is at a driving range. Perform a biomechanical analysis and provide force analysis and metrics for power, swing speed and technique.

Actors: Golfer, club, ball

Preconditions: Wearable sensors are in place. Active Bluetooth Network. Golfer is using a club during the activity.

Description
1. Biomechanical analysis (gyroscope, accelerometer, magnetometer, pressure sensor)
2. Determine the power of the swing as golfer makes contact with the ball (accelerometer)
3. Determine speed of the swing (gyroscope, accelerometer, magnetometer)
4. Determine location of the ball (proximity sensor)
5. Provide performance-related haptic and/or vibrational feedback to golfer (haptics module)
6. Provide contextual 3D motion-tracking animation showing golfer's swing and location of the ball.
7. Provide swing performance summary, power, technique, and speed. The use case terminates at this point.

Example 11: Provide Contextual Metrics Pertaining to Racket Swing Analysis, Swing Speed and Hitting Power of a Tennis Player Summary: A tennis player is in practice. Perform a biomechanical analysis and provide force analysis and metrics for power, swing speed and technique for both service and returns.

Actors: Racket, partner (person or machine), ball

Preconditions: Wearable sensors are in place. Active Bluetooth Network. Tennis player is using racket during the activity.

Description
1. Biomechanical analysis (gyroscope, accelerometer, magnetometer, pressure sensor)
2. Determine when tennis player makes contact with the ball and power of the swing (accelerometer)
3. Determine speed of the swing (gyroscope, accelerometer, magnetometer)
4. Determine location of the ball (proximity sensor)
5. Provide performance-related haptic and/or vibrational feedback to tennis player (haptics module)
6. Provide contextual 3D motion-tracking animation showing tennis player's swing and location of the ball.
7. Provide racket performance summary, power, technique, and speed.

IV. Conclusion

Although many of the embodiments are described above with respect to systems, devices, and methods for sports analytics, the technology is applicable to other applications and/or other approaches, such as research and rehabilitation. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or other embodiments without several of the features shown and described above with reference to FIGS. 1A-13B.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A system for evaluating athletic performance, the system comprising:
a plurality of garments each configured to be removably coupled to an athlete's body during athletic performance, wherein each of the garments comprises a receptacle configured to receive a wearable sensor device therein, each receptacle including an aperture;
a plurality of wearable sensor devices each configured to be removably received within a respective garment receptacle during athletic performance, wherein each of the wearable sensor devices comprises:
a motion sensor;
a first proximity sensor comprising an optical time-of-flight sensor configured to be aligned with the receptacle aperture when the wearable sensor device is received within the receptacle such that the optical time-of-flight sensor faces outwardly from the athlete's body and can transmit and receive optical signals through the aperture to obtain proximity measurements;
a rechargeable power source;
a haptics module configured to provide haptic feedback to the athlete; and
a first wireless communications component configured to communicate with one or more external devices;
one or more stationary sensor devices configured to be coupled to reference objects adjacent to an athletic performance site, each of the one or more stationary sensor devices comprising:
a second proximity sensor configured to detect an athlete's body or athletic equipment within a field of view of the second proximity sensor; and
a second wireless communications component configured to communicate with one or more external devices; and
a computing device communicatively coupled to the plurality of wearable sensor devices and the one or more stationary sensor devices, the computing device configured to:
receive first sensor data from each of the wearable sensor devices;
receive second sensor data from the one or more stationary sensor devices; and
based on the first and second sensor data, determine at least one performance parameter.

2. The system of claim 1, wherein the computing device is further configured to, based on the at least one performance parameter, cause the haptics module to provide haptic feedback to the athlete in real-time.

3. The system of claim 1, wherein the first proximity sensor comprises a time-of-flight optical sensor configured to determine a distance to objects relative to the wearable sensor device.

4. The system of claim 3, wherein the first proximity sensor comprises a light detection and ranging (LiDAR) sensor.

5. The system of claim 1, wherein each of the wearable sensor devices comprises a housing defining a housing aperture, and wherein the first proximity sensor is disposed within the housing and configured to transmit and receive optical signals through the housing aperture.

6. The system of claim 1, wherein:
the motion sensor comprises a first accelerometer;
the haptics module comprises a vibratory actuator; and
the first wireless communications component comprises a Bluetooth transceiver;
each of the wearable sensor devices further comprises a position sensor including at least one of a magnetometer or a gyroscope; and
each of the wearable sensor devices further comprises a vibration sensor including a second accelerometer.

7. The system of claim 1, wherein each wearable sensor device further comprises a vibration sensor, wherein the first sensor data includes vibration sensor data, and wherein the computing device is further configured to identify ball-striking events based at least in part on the vibration sensor data.

8. The system of claim 1, wherein the second proximity sensor comprises a short-range proximity sensor configured to detect objects within a first predetermined distance from the stationary sensor device, the stationary sensor device further comprising a third proximity sensor that is a long-range proximity sensor configured to detect objects further than the first predetermined distance from the stationary sensor device.

9. The system of claim 1, wherein the plurality of garments includes a plurality of sleeves configured to be worn over the athlete's arms and legs.

10. The system of claim 1, wherein the plurality of wearable sensor devices comprises at least 8 wearable sensor devices, and wherein the plurality of garments comprises at least 8 garments each having a corresponding receptacle configured to receive a corresponding wearable sensor device therein, each receptacle including an aperture.

11. The system of claim 1, wherein the computing device is further configured to:
generate, based on the received first and second sensor data, a 3D animation of the athlete's movement over time;
generate, based on the received first and second sensor data, one or more quantitative metrics characterizing the athlete's athletic performance; and
causing the 3D rendering animation and the one or more quantitative metrics to be displayed to a user via a display device.

12. The system of claim 1, wherein the computing device is further configured to:
generate, based on the received first and second sensor data, a measurement of the athlete's performance of a particular activity;
evaluating the measured performance of the particular activity to identify an incorrect motion; and
responsive to identifying the incorrect motion, causing one or more of the plurality of wearable sensor devices to output, via the haptics module, haptic feedback to the athlete.

13. A system for evaluating athletic performance, the system comprising:
a plurality of garments each configured to be removably coupled to an athlete's body during athletic performance, wherein each of the garments comprises a receptacle configured to receive a wearable sensor device therein, each receptacle including an aperture;
a plurality of wearable sensor devices each configured to be removably received within a respective garment receptacle during athletic performance, each of the wearable sensor devices including at least a first proximity sensor, wherein the first proximity sensor comprises an optical time-of-flight sensor configured to be aligned with the receptacle aperture when the wearable sensor device is received within the garment receptacle such that the optical time-of-flight sensor faces outwardly and can transmit and receive optical signals through the aperture to obtain proximity measurements;
one or more stationary equipment-mountable sensor devices configured to be coupled to reference objects adjacent to an athletic performance site, the stationary equipment-mountable sensor device(s) including at least a second proximity sensor; and
a computing device communicatively coupled to the plurality of wearable sensor devices and the equipment-mountable sensor device(s), the computing device configured to receive sensor data from each of the sensor devices and to determine at least one performance parameter.

14. The system of claim 13, wherein each of the wearable sensor devices further comprises at least one of: a gyroscope, an accelerometer, and a magnetometer.

15. The system of claim 13, wherein each of the wearable sensor devices each comprises a rechargeable power source.

16. The system of claim 13, wherein each of the wearable sensor devices each comprises a wireless transceiver.

17. The system of claim 16, wherein the wireless transceiver comprises a Bluetooth transceiver.

18. The system of claim 13, wherein the one or more equipment-mountable sensor devices each comprises at least one of: a proximity sensor and an accelerometer.

19. The system of claim 13, wherein the reference object to which the one or more equipment-mountable sensor devices are configured to be coupled comprises sports equipment.

20. The system of claim 19, wherein the sports equipment comprises a goal.

21. The system of claim 13, wherein the pluralities of devices are configured to communicate with one another via a mesh network.

22. The system of claim 13, wherein the plurality of devices are configured to communicate with one another via an extender device via a star network configuration.

23. The system of claim 13, wherein the pluralities of devices are configured to communicate with one another via a Bluetooth communications link.

24. The system of claim 13, wherein the computing device is further configured to generate a graphical representation of the athlete's performance.

25. The system of claim 13, wherein each of the wearable sensor devices comprises a haptics module configured to produce vibratory output.

* * * * *